(12) United States Patent
Khan

(10) Patent No.: US 9,670,446 B2
(45) Date of Patent: Jun. 6, 2017

(54) BIOREACTOR FOR THE CULTIVATION OF MAMMALIAN CELLS

(71) Applicant: Lonza Biologics PLC, Slough (GB)

(72) Inventor: Mohsan Khan, Watford (GB)

(73) Assignee: Lonza Biologics PLC, Slough (GB)

( * ) Notice: Subject to any disclaimer, the term of this patent is extended or adjusted under 35 U.S.C. 154(b) by 0 days.

(21) Appl. No.: 14/885,802

(22) Filed: Oct. 16, 2015

(65) Prior Publication Data

US 2016/0032232 A1    Feb. 4, 2016

Related U.S. Application Data

(62) Division of application No. 13/148,503, filed as application No. PCT/EP2010/000783 on Feb. 9, 2010.

(30) Foreign Application Priority Data

Feb. 9, 2009  (EP) .................................... 09001755

(51) Int. Cl.
| C12M 3/02 | (2006.01) |
|---|---|
| C12M 1/00 | (2006.01) |
| C12M 1/06 | (2006.01) |
| C12N 5/00 | (2006.01) |
| C12M 3/00 | (2006.01) |

(52) U.S. Cl.
CPC ............ *C12M 23/58* (2013.01); *C12M 21/08* (2013.01); *C12M 27/02* (2013.01); *C12M 27/08* (2013.01); *C12M 27/20* (2013.01); *C12M 29/06* (2013.01); *C12N 5/00* (2013.01); *C12N 2527/00* (2013.01)

(58) Field of Classification Search
CPC ......... C12M 27/08; C12M 27/02; C12N 5/00; C12N 2527/00
USPC ........................................................ 435/325
See application file for complete search history.

(56) References Cited

U.S. PATENT DOCUMENTS

| 4,378,436 A | 3/1983 | Heine et al. |
|---|---|---|
| 5,075,234 A | 12/1991 | Tunac |
| 5,633,165 A | 5/1997 | Swartz |
| 5,882,913 A | 3/1999 | Slavicek et al. |
| 5,888,806 A | 3/1999 | Nguyen |
| 5,972,661 A | 10/1999 | Kubera et al. |
| 5,972,695 A | 10/1999 | Murofushi et al. |
| 6,395,516 B1 | 5/2002 | Nienow et al. |
| 2001/0055237 A1 | 12/2001 | Kubera et al. |
| 2005/0239199 A1 | 10/2005 | Kunas et al. |

(Continued)

FOREIGN PATENT DOCUMENTS

| CN | 1326814 A | 12/2001 |
|---|---|---|
| CN | 1560222 A | 1/2005 |

(Continued)

OTHER PUBLICATIONS

Birch et al. "Antibody production". Advanced Drug Delivery Reviews, vol. 58 (May 22, 2006), pp. 671-685.*

(Continued)

*Primary Examiner* — William H Beisner
(74) *Attorney, Agent, or Firm* — Crowell & Moring LLP

(57) ABSTRACT

The present invention relates to large-scale bioreactors having at least two impellers, large-scale bioreactor systems and methods for the large scale cultivation and propagation of mammalian cells using these bioreactors.

26 Claims, 2 Drawing Sheets

(56) References Cited

U.S. PATENT DOCUMENTS

| | | | |
|---|---|---|---|
| 2007/0065927 A1 | 3/2007 | Brahmbhatt | |
| 2007/0172945 A1* | 7/2007 | O'Kennedy | C12M 29/02 |
| | | | 435/325 |
| 2008/0068920 A1 | 3/2008 | Galliher et al. | |
| 2008/0233631 A1 | 9/2008 | Higashiyama | |
| 2009/0035856 A1 | 2/2009 | Galliher et al. | |
| 2009/0208390 A1 | 8/2009 | Gobby et al. | |
| 2016/0040110 A1 | 2/2016 | Khan | |

FOREIGN PATENT DOCUMENTS

| | | | |
|---|---|---|---|
| CN | 1578830 A | | 2/2005 |
| CN | 1854286 A | | 11/2006 |
| EP | 0025571 A | | 3/1981 |
| EP | 0143560 | * | 10/1984 |
| EP | 0477818 A | | 4/1992 |
| EP | 1 120 153 A2 | | 8/2001 |
| EP | 1167511 A | | 1/2002 |
| EP | 2039754 A | | 3/2009 |
| JP | 2006-503687 | | 2/2006 |
| JP | 2008-182899 | | 8/2008 |
| JP | 2008-536686 | | 9/2008 |
| JP | 4260425 B2 | | 4/2009 |
| JP | 2012-517217 A | | 8/2012 |
| WO | WO 03/057818 A | | 7/2003 |
| WO | WO 2004/025125 A2 | | 3/2004 |
| WO | WO 2005/104706 A2 | | 11/2005 |
| WO | WO 2007/087438 A | | 8/2007 |
| WO | WO 2007/129023 A1 | | 11/2007 |
| WO | WO 2008/088371 A2 | | 7/2008 |

OTHER PUBLICATIONS

Mahmoudi, S., Velocity and Mixing Characteristics of Stirred Vessels With Two Impellers, Mechanical Engineering Department, King's College London (1993).

Notice of Reasons for Rejection dated Jul. 30, 2013 in corresponding Japanese Patent Application No. 2011-548618 (with English language translation).

Jia et al., A Bioreactor System Based on a Novel Oxygen Transfer Method, Bioprocess International, pp. 66-71, Jun. 2008.

Whitford "NS0 Serum-Free Culture and Applications", Bioprocess International, pp. 36-47, Dec. 2003.

Gill et al., "Quantification of Power Consumption and Oxygen Transfer Characteristics of a Stirred Miniature Bioreactor for Predictive Fermentation Scale-Up", Biotechnology and Bioengineering, vol. 100, No. 6, Aug. 15, 2008.

Verpoorte et al., "Plant Cell Biotechnology for the Production of Alkaloids: Present Status and Prospects", Journal of Natural Products, vol. 56, No. 2, pp. 186-207, Feb. 1993.

International Search Report dated Mar. 24, 2010, issued in corresponding international application No. PCT/EP2010/000783.

Office Action dated Sep. 20, 2012 in corresponding Chinese Patent Application No. 201080007208.6 (with English language translation).

Ningning Ma, et al., "Fabrication and Use of a Transient Contractional Flow Device to Quantify the Sensitivity of Mammalian and Insect Cells to Hydrodynamic Forces", Biotechnology and Bioengineering, Nov. 20, 2002, vol. 80, No. 4, pp. 428-437.

Ningning Ma, et al., "Fabrication and Use of a Transient Contractional Flow Device to Quantify the Sensitivity of Mammalian and Insect Cells to Hydrodynamic Forces", Biotechnology and Bioengineering, Feb. 5, 2003; vol. 81, No. 3, p. 379.

European Office Action issued in European Application No. 10 704 752.4-1501 dated May 31, 2016 (twelve (12) pages).

Alvin W. Nienow, "Reactor Engineering in Large Scale Animal Cell Culture", Cytotechnology, 2006, vol. 50, pp. 9-33.

Frans W. J. M.M. Hoeks, "Scale-up of Stirring as Foam Disruption (SAFD) to Industrial Scale", J. Ind. Microbiol Biotechnol, 2003, vol. 30, pp. 118-128.

Alvin W. Nienow, "Technical Paper: Stirred Bioreactor Engineering for Production Scale, Low Viscosity Aerobic Fermentations: Part 2", 2012 (Eleven (11) pages).

English translation of Japanese Office Action dated Jul. 30, 2013 (Three (3) pages).

Japanese language Office Action with English translation dated Jun. 3, 2014 (Eight (8) pages).

Chinese language Office Action dated Dec. 22, 2014 (Six (6) pages).

Japanese language Office Action dated Sep. 29, 2015 (Six (6) pages).

Chinese language Office Action with English translation dated Feb. 25, 2016 (Fifteen (15) pages).

Chinese language Office Action dated May 12, 2016 (Six (6) pages).

Japanese Office Action with English translation dated Jun. 7, 2016 (Six (6) pages).

Japanese Office Action Reply dated Oct. 3, 2014 (Twelve (12) pages).

Japanese Office Action Reply dated Mar. 25, 2016 (Fifty-six (56) pages).

* cited by examiner

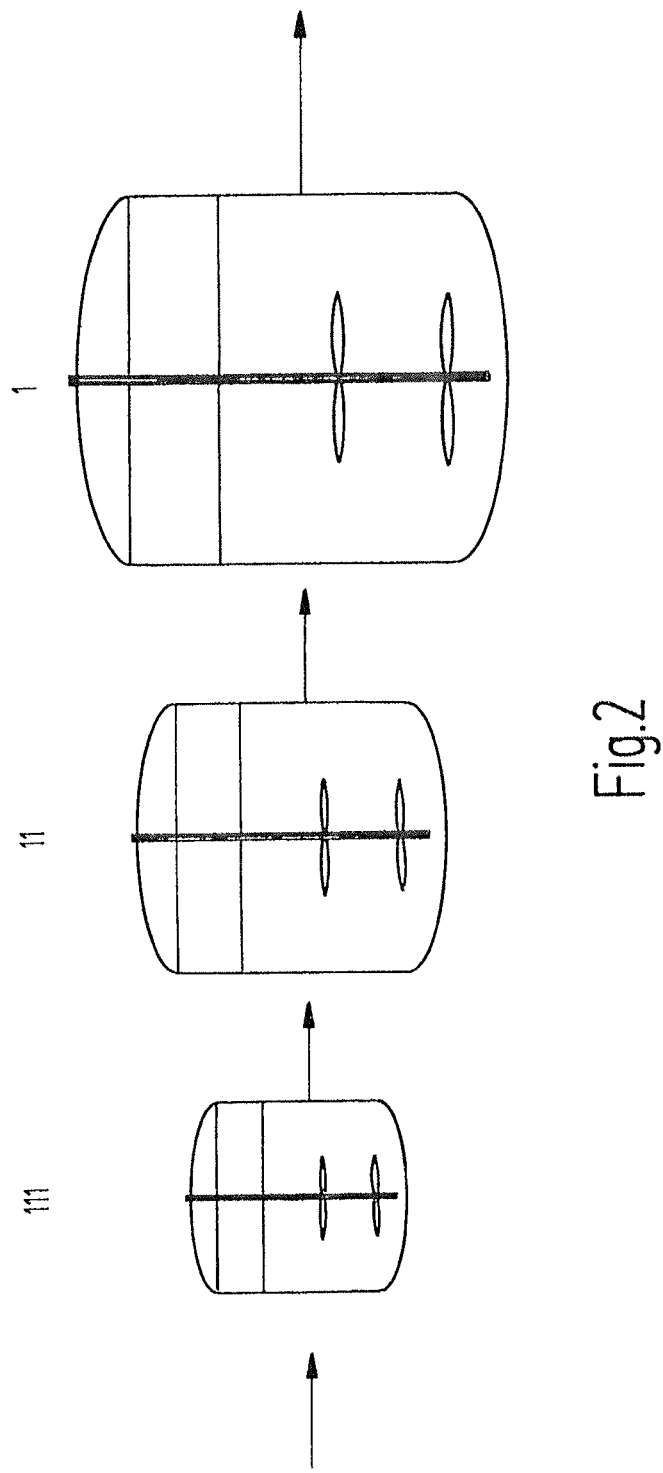

US 9,670,446 B2

BIOREACTOR FOR THE CULTIVATION OF MAMMALIAN CELLS

CROSS REFERENCE TO RELATED APPLICATIONS

This application is a divisional application of U.S. patent application Ser. No. 13/148,503, filed Aug. 23, 2011, which is a national stage application of International Application No. PCT/EP2010/000783, filed Feb. 9, 2010, which claims priority to European Application No. 09001755.9, filed Feb. 9, 2009, each of which is incorporated by reference in its entirety.

FIELD OF THE INVENTION

The present invention relates to bioreactors and methods for the large scale cultivation of mammalian cells using these bioreactors.

BACKGROUND OF THE INVENTION

It is important in mammalian cell culture processes to maintain the physicochemical environment in view of dissolved oxygen, culture pH, temperature and shear sensitivity. Also the maintenance of the nutritional environment is important. The maintenance of the cultivation conditions limits the possibility to perform large scale culturing of mammalian cells. Especially concentration gradients can inhibit the cell growth of mammalian cells in large-scale bioreactors.

One of the objects of the present invention is to provide bioreactors and methods, which allow the cultivation of mammalian cells in large scale volumes. Furthermore, it is an object of the present invention to provide bioreactors and methods, which allow the cultivation of mammalian cells under optimal conditions, even if grown in large scale volumes and therefore allow a process performance and product quality independent of the size of the bioreactor.

It is an object of the present invention to provide large-scale bioreactors which allow the cultivation of mammalian cells in a homogenous environment with respect to process parameters such as pH, dissolved oxygen tension (DOT) and temperature, maintaining a well mixed cell suspension and blending nutrient feeds within the bioreactor.

Furthermore it is an object of the present invention to provide devices and methods which allow the production of mammalian cells and products of the mammalian cells, especially proteins, peptides, antibiotics or amino acids, synthesised by the mammalian cells, in a large-scale manner.

The present invention solves the technical problems underlying the present invention by the provision of bioreactors, bioreactor systems and methods for the cultivation of eukaryotic cells, especially of mammalian cells, according to the claims.

The present invention solves the technical problem underlying the present invention especially by the provision of a bioreactor for the cultivation of mammalian cells, characterised in that said bioreactor has at least two impellers. Furthermore, the present invention solves the technical problem underlying the present invention by the provision of a method for the cultivation and propagation of mammalian cells characterised in that at least one mammalian cell is cultivated under suitable conditions and in a suitable culture medium in a bioreactor, which has at least two impellers. Furthermore, the present invention solves the technical problems underlying the present invention by the provision of a bioreactor system for the cultivation of mammalian cells characterised in that a) a first bioreactor with a volume of at least 500 l is connected with b) a second bioreactor with a volume of at least 2000 l, which has a volume greater than the first bioreactor and wherein the second bioreactor with a volume of at least 2000 l is connected with c) a third bioreactor having at least two impellers and a volume of at least 10 000 l, which has a volume greater than the second bioreactor.

The present invention solves the technical problem underlying the present invention furthermore by the provision of a method to cultivate and propagate mammalian cells, characterised in that a) at least one mammalian cell is cultivated under suitable conditions and in a suitable culture medium in a first bioreactor with a volume of at least 500 l, b) the medium containing the cells obtained by propagation of the at least one mammalian cell is transferred into a second bioreactor with a volume of at least 2000 l, c) the transferred cells are cultivated in the second bioreactor with a volume of at least 2000 l, d) the medium containing the cells obtained in step c) is transferred into a third bioreactor with a volume of at least 10 000 l and e) the transferred cells are cultivated in the third bioreactor with a volume of at least 10 000 l.

According to the invention, the cultivated cells are eukaryotic cells, preferably animal cells, more preferably mammalian cells. The mammalian cells can be for example human cell lines, mouse myeloma (NS0)-cell lines, Chinese hamster ovary (CHO)-cell lines or hybridoma-cell lines. Preferably the mammalian cells are CHO-cell lines.

Preferably the cultivated cells are used to produce antibodies, more preferably monoclonal antibodies, and/or recombinant proteins, more preferably recombinant proteins for therapeutic use. Of course the cells may produce peptides, amino acids, fatty acids or other useful biochemical intermediates or metabolites. According to the invention the target concentration of the proteins produced by the cultivated cells is more than 0.5 g/l, preferably more than 2.0 g/l and most preferred more than 10.0 g/l. The method according to the invention can be used as a batch or in a fed-batch process. Although the cell-culture-medium used in the method according to the invention is preferably protein free medium, the design does not exclude the use of protein containing streams.

DETAILED DESCRIPTION OF THE INVENTION

According to the invention a bioreactor is a biocompatible tank or vessel having additional equipment, for example impellers, baffles, spargers and/or ports, which specifically allows for the cultivation and propagation of mammalian cells. Preferably the tank or vessel is in the form of a tube, having on both ends of the tube, which build preferably the top and the bottom of the tank, plates. The plates are called head plate and base plate. In a particularly preferred embodiment of the present invention the base plate is an American Society of Mechanical Engineers Flanged and Dished (ASME F&D) designed base plate. The head-plate design preferably accommodates a manway or is preferably a flanged head plate to allow access/removal of the impellers.

The total tank height is the tangential line from the inner tank side of the base to the inner tank side of the head of the tank.

The freeboard height is defined as the length of straight side above the liquid head when the bioreactor is filled to it's operating volume. A minimum freeboard height is necessary taking into account the extent of foam build up during operation, gas hold up at maximum allowed agitation and aeration and errors in metering liquid.

The bioreactor according to the invention has a volume of preferably at least 500 l, more preferably of at least 1000 l, more preferably of at least 4000 l, even more preferably of at least 10 000 l, even more preferably of at least 20 000 l. Most preferably the bioreactor according to the invention has a volume of 1000 l, 1307 l, 4000 l, 5398 l, 20 000 l or 27 934 l.

Preferably, the bioreactor has a maximum volume of 100 000 l, more preferably the bioreactor has a maximum volume of 50 000 l, most preferably the bioreactor has a maximum volume of 30 000 l.

The design of the bioreactors according to the present invention ensures a homogenous environment with respect to process parameters such as pH, dissolved oxygen tension (DOT) and temperature, maintaining a well mixed cell suspension and blending nutrient feeds within the bioreactor. This provides the necessary physicochemical environment for optimal cell growth, product accumulation and product quality. The design of the bioreactors according to the present invention furthermore ensures the maintenance of geometric similarity. This allows a scale down model to be developed at 12 liter laboratory and 500 liter pilot scales.

The bioreactor for the cultivation of mammalian cells according to the invention has at least two impellers. More preferably, the bioreactor has two impellers, even more preferably a top impeller and a bottom impeller.

The bioreactor for the cultivation of mammalian cells according to the invention has preferably at least one top impeller and at least one bottom impeller, wherein the top impeller is preferably a hydrofoil impeller.

The bioreactor for the cultivation of mammalian cells according to the invention has preferably at least one top impeller and at least one bottom impeller, wherein the top impeller is a hydrofoil impeller.

The bioreactor for the cultivation of mammalian cells according to the invention has preferably a volume of at least 1000 l and at least one top impeller and at least one bottom impeller, wherein the top impeller is a hydrofoil impeller.

The bioreactor for the cultivation of mammalian cells according to the invention has preferably a volume of at least 4000 l and at least one top impeller and at least one bottom impeller, wherein the top impeller is preferably a hydrofoil impeller.

The bioreactor for the cultivation of mammalian cells according to the invention has preferably a volume of at least 4000 l and at least one top impeller and at least one bottom impeller, wherein the top impeller is a hydrofoil impeller.

In a preferred embodiment of the invention the top impeller is a hydrofoil impeller. The top impeller can be used preferably to provide strong bulk mixing.

In a preferred embodiment of the invention the bottom impeller is a hydrofoil impeller. In a preferred embodiment of the invention the top impeller and the bottom impeller are a hydrofoil impeller.

In a preferred embodiment of the invention at least the top impeller is a hydrofoil impeller. In a preferred embodiment of the invention all impellers are hydrofoil impellers.

According to a preferred embodiment of the invention the bottom impeller is a high-solidity pitch-blade impeller or a high-solidity hydrofoil impeller. The bottom impeller can be used preferably for the dissipation of sparged gas.

Preferably, the hydrofoil impellers provide much greater liquid motion, resulting in a greater bulk-mixing, for a given amount of power input. This can also depend of the flow number ($N_q$).

Preferably, non-hydrofoil impellers can provide liquid motion but at greater power inputs. This can have consequences on the health of shear-sensitive mammalian cells.

In a preferred embodiment of the invention the hydrofoil impeller is a down-flowing impeller or a up-flowing impeller.

In a preferred embodiment of the invention the top impeller is a down-flowing impeller. In a preferred embodiment of the invention the top impeller is a down-flowing axial hydrofoil impeller.

In a preferred embodiment of the invention the pulling down characteristics of the top impeller are used to mix the well aerated liquid surface with the liquid bulk.

In a preferred embodiment of the invention the hydrofoil impeller is a high efficiency hydrofoil impeller. In a preferred embodiment of the invention the hydrofoil impeller is a Chemineer—model SC-3 impeller, a LIGHTNIN—model A310 or A510 impeller, a Promix—model PHF series impeller or a Cleaveland Eastern Mixers impeller.

In a preferred embodiment of the invention the top impeller is a high efficiency hydrofoil impeller. In a preferred embodiment of the invention the top impeller is a Chemineer—model SC-3 impeller, a LIGHTNIN—model A310 or A510 impeller, a Promix—model PHF series impeller or a Cleaveland Eastern Mixers impeller.

The top impeller is preferably a three-bladed hydrofoil design impeller, for example a A310-type impeller from LIGHTNIN. The bottom impeller is preferably a four-pitched-bladed high-solidity impeller, for example of the A315-type from LIGHTNIN. The impeller to tank diameter ratio of the top impeller ($D_{top}/T$) and/or of the bottom impeller ($D_{bottom}/T$) is preferably at least 0.35 and at most 0.55, more preferably at least 0.40 and at most 0.48, and most preferably at least 0.44, and at most 0.46. A diameter greater than 0.5 results in disruption in axial flow, hence poor agitation and aeration.

The top impeller power number ($N_p$) is preferably at least 0.1 and at most 0.9, more preferably at least 0.25 and at most 0.35, most preferably 0.3. The top impeller flow number ($N_q$) is preferably at least 0.4 and at most 0.9, more preferably at least 0.50 and at most 0.60, most preferably 0.56. The bottom impeller power number ($N_p$) is preferably at least 0.5 and at most 0.9, more preferably at least 0.70 and at most 0.80, most preferably 0.75. The bottom impeller flow number ($N_q$) is preferably at least 0.50 and at most 0.85, more preferably at least 0.70 and at most 0.80, most preferably 0.73.

The impeller power number ($N_p$) is a measure of an impeller efficiency to impart the kinetic energy of the rotating impeller blades to the fluid. It is important in quantifying the gas dispersion. The impeller flow number ($N_q$) is a measure of pumping ability of the impeller and is important in quantifying fluid bulk movement.

The agitation rate of the at least two impellers is dependent on the scale. However, in a particularly preferred embodiment of the invention the agitation rate of the at least two impellers is at most 200 rounds per minute (rpm), more preferably at most 165 rpm.

The impeller spacing ($D_s$) is the space between the at least two impellers. It is in a particularly preferred embodiment of the invention at least 1× the diameter of the bottom impeller ($D_{bottom}$) and at most 2×$D_{bottom}$, more preferably it is $1.229 \times D_{bottom}$ or $2 \times D_{bottom}$. This will allow both impellers to remain submerged at the lowest post-inoculation volume.

The liquid height above the upper impeller ($D_o$) is in a particularly preferred embodiment of the invention at least $0.3 \times$ the diameter of the top impeller ($D_{top}$) and at most $2.5 \times D_{top}$. More preferably it is at least $0.5 \times D_{top}$ and at most $2.0 \times D_{top}$.

The bottom clearance ($D_c$) is the clearance between the tank bottom and the centre-line of the bottom impeller. In a particularly preferred embodiment of the invention it is at least $0.35 \times D_{bottom}$, more preferably it is either $0.4 \times D_{bottom}$ or $0.75 \times D_{bottom}$.

The design of the impellers in the bioreactor according to the present invention provides optimal hydrodynamic characteristics in terms of bulk mixing, gas dispersion and low shear. The mammalian cells are kept in a homogeneous suspension by agitation via the impeller system according to the present invention.

The design of the impellers in the bioreactor according to the present invention provides rapid mixing, maintain homogeneity, maintain mammalian cells in suspension and gas bubble dispersion. The design of the impellers in the bioreactor according to the present invention minimises cell damage through shear forces originating from impeller geometry and eddies or vortices created behind the impeller blades.

In a particularly preferred embodiment of the present invention, the at least two impellers are a top driven agitator system.

The supply of air, especially compressed air, or specific gases, preferably oxygen, nitrogen and/or $CO_2$ is realised preferably through at least one sparger.

The bioreactor according to the invention has preferably at least one sparger, more preferably the bioreactor has one sparger or two spargers. The bioreactor according to the invention has preferably two spargers. Preferably the bioreactor has at least one sparger with a pipe-geometry. Preferably the at least one sparger is of the flute-type or is a sintered sparger. Preferably the at least one sparger is of the flute-type. In particularly preferred embodiment of the present invention a crescent pipe is explored. The curvature of the crescent is preferably $0.8 \times D_{bottom}$. In order to aid installation and removal from side ports of the bioreactor the crescent circumference is preferably 240° of the complete circumference of $0.8 \times D_{bottom}$ ring.

The at least one sparger provides sufficient oxygen mass transfer (characterised by $K_L a$) to meet the oxygen demand of the culture. The at least one sparger provides a $K_L a$ up to $20\ h^{-1}$ for cultures reaching up to $20 \times 10^6$ cells per ml with an oxygen uptake rate of 5 mmol/l per hour. Two spargers used as a dual sparger system allow the removal of dissolved $CO_2$ and control of dissolved oxygen tension (DOT). Fluted spargers offer the benefits of easier cleaning in place (CIP) and sterilisation in place (SIP), aids with $dCO_2$ stripping and reduced operational costs as it is multiple use. Sintered spargers provide higher $K_L a$ values. The lower intrinsic $K_L a$ value with the fluted sparge design can be compensated by the use of oxygen enriched air. The gas flow rates are scaled up on the basis of constant superficial gas velocity.

It is important in large scale cultivation of mammalian cells to maintain a homogenous physicochemical environment in terms of dissolved oxygen, culture pH, and temperature, and dissolved $CO_2$, nutrient and metabolite concentration gradients. Whilst ensuring the physicochemical environment is homogenous through using appropriate agitation and aeration, it is important to ensure the selected operating agitation and aeration conditions do not produce adverse shear environment. The appropriate balance between ensuring homogenous environment that will promote good cell growth and productivity of mammalian cell culture processes whilst minimising the adverse effects of shear environment is dealt with in this invention. This is achieved through prescribing specific bioreactor geometries, impeller design and positioning, sparger design and positioning and specific operating limits for agitation and aeration rates.

The major damage to mammalian cells in stirred and sparged bioreactors comes from interfacial shear. Interfacial shear occurs as sparged gas bubbles coalesce and burst [ref: Ma N, Koelling K W, Chalmers J J. Biotechnol Bioeng. 2002 Nov. 20; 80(4):428-37. Erratum in: Biotechnol Bioeng. 2003 Feb. 5; 81(3):379]. Thus minimising sparged gas flows and excessive build up of foam is desirable. The interfacial shear can be minimised through a combination of approaches first by promoting surface aeration through good mixing of the liquid surface with the liquid bulk and secondly higher oxygen driving force by segregated oxygenation of cultures through the preferably two spargers.

The prescribed positioning of the hydrofoil impeller, particularly the liquid height above the upper impeller, $D_O$ preferably being around $0.5 \times D_{top}$, below the liquid surface can aid strong and continuous exchange of the liquid surface with the liquid bulk thereby mixing the well oxygenated liquid surface with less oxygenated liquid bulk. The prescribed impeller spacing, preferably being $D_s = 1 \times D_{bottom}$ to $2 \times D_{bottom}$ can permit the down-flow of liquid generated by the upper impeller to feed fluid flow into the lower impeller thereby ensuring the whole fluid bulk is well-mixed and separate mixing zones are not made. The prescribed impeller bottom clearance, preferably being $D_c = 0.35 \times D$ to $0.75 \times D$ can ensure that the bulk flow is able to deflect off the curved ASME F&D base and rise upwards along the walls of the bioreactor.

The segregation of the 'on-demand' oxygenated sparged gas through the control sparger from the non-oxygenated sparged gases (such as $CO_2$, air and nitrogen ballasts) through a ballast sparger can allow greater residence time and path length of highly oxygenated sparge gas bubbles in the fluid bulk before disengaging out of the fluid bulk and into the headspace. This can permit greater oxygen transfer rates to be provided for a given volumetric mass transfer coefficient, $k_{La}$. The residence time and path length of the sparged gas bubbles can be extended further through specifying down-flowing axial hydrofoil impellers that continuingly pull the liquid surface and liquid bulk down.

The bioreactor according to the invention has preferably at least one baffle, more preferably at least two baffles. The bioreactor according to the invention has most preferably four baffles.

Baffles are vertical radially located plates. Baffles are used to prevent the formation of a funnel or vortex formation.

In a preferred embodiment of the invention, the length of the at least one baffle is $1.1 \times$ the total straight height (H) of the bioreactor. The width of the baffle (W) is preferably $0.1 \times$ the internal diameter of the tank (T). The baffle clearance ($W_c$) is preferably $0.01 \times$ the internal diameter of the tank (T). The height of at least one baffle ($H_{baffle}$) is preferably $1.1 \times$ the total straight height (H)—the height of the bioreactor-head ($H_h$). Therefore $H_{baffle}$ is preferably calculated according to the formula $H_{baffle} = 1.1 \times H - H_h$.

The thickness of the at least one baffle is not specified but the thickness needs to ensure rigidity to the radial component of the fluid flow. Additionally thickness needs to ensure the baffle plates are not warped during SIP thereby affecting the baffle to tank wall clearance.

The bioreactor according to the invention has preferably at least two ports for alkali addition. More preferably, the bioreactor has two ports for alkali addition. Most preferably, the bioreactor has two ports for alkali addition, wherein the first port is located at the central line of the bottom impeller and the second port is located at the central line of the top impeller. Preferably the pH probes are located diametrically opposite the alkali addition points into the bioreactor.

In a preferred embodiment of the invention, the bioreactor has a volume of 1000 l. The head volume ($V_h$) of a 1000 l bioreactor is preferably at least 45 l and at most 65 l, more preferably the head volume is 55 l. The base volume ($V_b$) of the 1000 l bioreactor is preferably at least 45 l and at most 65 l, more preferably the base volume is 55 l. The tank internal diameter (T) of the 1000 l bioreactor according to the invention is preferably at least 850 mm and at most 900 mm, more preferably the tank internal diameter is 864 mm. The tank cross-sectional area (A) of the 1000 l bioreactor according to the invention is preferably at least 0.55 m$^2$ and at most 0.65 m$^2$, more preferably the tank cross-sectional area is 0.586 m$^2$. The head height ($H_h$), which is the height of the head-plate, and/or the base height ($H_b$), which is the height of the base-plate, of the bioreactor with a volume of 1000 l according to the invention is preferably at least 120 mm and at most 180 mm, more preferably the head height and/or the base height is 151 mm. The total tank height of the 1000 l bioreactor according to the invention is preferably at least 2000 mm and at most 2600 mm, more preferably the total tank height is 2347 mm. The top impeller diameter ($D_{top}$) and/or the bottom impeller diameter ($D_{bottom}$) of the 1000 l bioreactor according to the invention is preferably at least 350 mm and at most 400 mm, more preferably the top impeller diameter and/or the bottom impeller diameter is 381 mm. The clearance between the tank bottom and centre-line of the bottom impeller ($D_c$) is for the 1000 l bioreactor according to the invention, preferably at least 120 mm and at most 180 mm, more preferably the clearance is 152 mm. The distance between the at least two impellers, also known as impeller separation ($D_s$) is for the 1000 l bioreactor, according to the invention, preferably at least 730 and at most 790 mm, more preferably the impeller separation is 762 mm. The impeller shaft diameter for the 1000 l bioreactor according to the invention is preferably at least 102 mm and at most 152 mm. If the 1000 l bioreactor according to the invention has baffles, the length of the baffles is preferably at least 2000 mm and at most 2400 mm, more preferably the length is 2250 mm. The width of the baffles for the 1000 l bioreactor according to the invention is preferably at least 70 mm and at most 100 mm, more preferably the width is 86 mm. The baffle clearance for the 1000 l bioreactor according to the invention is preferably at least 7 mm and at most 11 mm, more preferably the baffle clearance is 9 mm. The baffle height ($H_{baffle}$) for the 1000 l bioreactor according to the invention is preferably at least 2000 mm and at most 2200 mm, more preferably the baffle height is 2099 mm. The 1000 l bioreactor according to the invention has preferably at least one sparger, more preferably it has one sparger. The at least one sparger of the 1000 l bioreactor according to the invention has preferably an orifice- or pore-size of at least 1.5 mm and at most 2.5 mm, more preferably the orifice- or pore-size is 2 mm. The orifice- or pore-number is preferably at least 20 and at most 40, more preferably the orifice- or pore-number is 30. The sparger length ($S_L$ is preferably at least 150 mm and at most 550 mm, more preferably the sparger length is 305 mm. The sparger to tank bottom clearance ($S_c$) of the 1000 l bioreactor according to the invention is preferably at least 50 mm and at most 75 mm, more preferably the sparger to tank bottom clearance is 64 mm. The sparger to bottom impeller clearance ($D_c$–$S_c$) of the 1000 l bioreactor according to the invention is preferably at least 75 mm and at most 100 mm, more preferably the sparger to bottom impeller clearance is 88 mm.

In a preferred embodiment of the invention, the bioreactor has a volume of 4000 l. The head volume ($V_h$) of a 4000 l bioreactor is preferably at least 340 l and at most 370 l, more preferably the head volume is 359 l. The base volume ($V_b$) of the 4000 l bioreactor is preferably at least 340 l and at most 370 l, more preferably the base volume is 359 l. The tank internal diameter (T) of the 4000 l bioreactor according to the invention is preferably at least 1600 mm and at most 1650 mm, more preferably the tank internal diameter is 1626 mm. The tank cross-sectional area (A) of the 4000 l bioreactor according to the invention is preferably at least 1.90 m$^2$ and at most 2.30 m$^2$, more preferably the tank cross-sectional area is 2.076 m$^2$. The head height ($H_h$) and/or the base height ($H_b$) of the bioreactor with a volume of 4000 l according to the invention is preferably at least 260 mm and at most 300 mm, more preferably the head height and/or the base height is 282 mm. The total tank height of the 4000 l bioreactor according to the invention is preferably at least 2300 mm and at most 3100 mm, more preferably the total tank height is 2817 mm. The top impeller diameter ($D_{top}$) and/or the bottom impeller diameter ($D_{bottom}$) of the 4000 l bioreactor according to the invention is preferably at least 680 mm and at most 740 mm, more preferably the top impeller diameter and/or the bottom impeller diameter is 710 mm. The clearance between the tank bottom and centre line of the bottom impeller ($D_c$) is for the 4000 l bioreactor according to the invention, preferably at least 500 mm and at most 560 mm, more preferably the clearance is 531 mm. The distance between the at least two impellers, also known as impeller separation ($D_s$) is for the 4000 l bioreactor, according to the invention, preferably at least 840 mm and at most 900 mm, more preferably the impeller separation is 872 mm. The impeller shaft diameter for the 4000 l bioreactor according to the invention is preferably at least 51 mm and at most 64 mm. If the 4000 l bioreactor according to the invention has baffles, the length of the baffles is preferably at least 2200 mm and at most 2600 mm, more preferably the length is 2477 mm. The width of the baffles for the 4000 l bioreactor according to the invention is preferably at least 150 mm and at most 180 mm, more preferably the width is 163 mm. The baffle clearance is for the 4000 l bioreactor according to the invention preferably at least 12 mm and at most 20 mm, more preferably the baffle clearance is 16 mm. The baffle height ($H_{baffle}$) for the 4000 l bioreactor according to the invention is preferably at least 2100 mm and at most 2300 mm, more preferably the baffle height is 2195 mm. The 4000 l bioreactor according to the invention has preferably at least one sparger, more preferably it has one sparger. The at least one sparger of the 4000 l bioreactor according to the invention has preferably an orifice- or pore-size of at least 1.5 mm and at most 2.5 mm, more preferably the orifice- or pore-size is 2 mm. The orifice- or pore-number for the 4000 l bioreactor according to the invention is preferably at least 80 and at most 120, more preferably the orifice- or pore-number is 100. The sparger length ($S_L$) is preferably at least 250 mm and at most 800 mm, more preferably the sparger length is 568 mm. The sparger to tank bottom clearance ($S_c$) of the 4000 l bioreactor according to the invention is preferably at least 315 mm and at most 360 mm, more preferably the sparger to tank bottom clearance is 337 mm. The sparger to bottom impeller clearance ($D_c$–$S_c$) of the 1000 l bioreactor according to the invention is preferably at least 180 mm and at most 205 mm, more preferably the sparger to bottom impeller clearance is 194 mm.

In a preferred embodiment of the invention, the bioreactor has a volume of 20 000 l. The head volume ($V_h$) of a 20 000 l bioreactor is preferably at least 1600 l and at most 2000 l, more preferably the head volume is 1803 l. The base volume ($V_b$) of the 20 000 l bioreactor is preferably at least 1600 l and at most 2000 l, more preferably the base volume is 1803 l. The tank internal diameter (T) of the 20 000 l bioreactor according to the invention is preferably at least 2500 mm and at most 3000 mm, more preferably the tank internal diameter is 2794 mm. The tank cross-sectional area (A) of the 20 000 l bioreactor according to the invention is preferably at least 5.8 $m^2$ and at most 6.5 $m^2$, more preferably the tank cross-sectional area is 6.131 $m^2$. The head height ($H_h$) and/or the base height ($H_b$) of the bioreactor with a volume of 20 000 l according to the invention is preferably at least 460 mm and at most 500 mm, more preferably the head height and/or the base height is 485 mm. The total tank height of the 20 000 l bioreactor according to the invention is preferably at least 4800 mm and at most 5100 mm, more preferably the total tank height is 4933 mm. The top impeller diameter ($D_{top}$) and/or the bottom impeller diameter ($D_{bottom}$) of the 20 000 l bioreactor according to the invention is preferably at least 1100 mm and at most 1300 mm, more preferably the top impeller diameter and/or the bottom impeller diameter is 1219 mm. The clearance between the tank bottom and centre line of the bottom impeller ($D_c$) is for the 20 000 l bioreactor according to the invention, preferably at least 890 mm and at most 945 mm, more preferably the clearance is 913 mm. The distance between the at least two impellers, also known as impeller separation ($D_s$) is for the 20 000 l bioreactor, according to the invention, preferably at least 1200 mm and at most 1700 mm, more preferably the impeller separation is 1498 mm. The impeller shaft diameter for the 20 000 l bioreactor according to the invention is preferably at least 51 mm and at most 64 mm. If the 20 000 l bioreactor according to the invention has baffles, the length of the baffles is preferably at least 4000 mm and at most 4600 mm, more preferably the length is 4365 mm. The width of the baffles for the 20 000 l bioreactor, according to the invention, is preferably at least 260 mm and at most 290 mm, more preferably the width is 279 mm. The baffle clearance for the 20 000 l bioreactor, according to the invention, is preferably at least 20 mm and at most 35 mm, more preferably the baffle clearance is 28 mm. The baffle height ($H_{baffle}$) for the 20 000 l bioreactor according to the invention is preferably at least 3600 mm and at most 4050 mm, more preferably the baffle height is 3882 mm. The 20 000 l bioreactor according to the invention has preferably at least one sparger, more preferably it has two spargers. If the 20 000 l bioreactor according to the invention has two spargers one is preferably a control sparger and one is preferably a ballast sparger. The control sparger for the 20 000 l bioreactor according to the invention has preferably an orifice- or pore-size of at least 3 mm and at most 5 mm, more preferably the orifice- or pore-size is 4 mm. The ballast sparger for the 20 000 l bioreactor according to the invention has preferably an orifice- or pore-size of at least 5 mm and at most 7 mm, more preferably the orifice- or pore-size is 6 mm. The orifice/pore number of the control sparger for the 20 000 l bioreactor according to the invention is preferably at least 230 and at most 270, more preferably the orifice- or pore-number is 250. The orifice-pore-number of the ballast sparger for the 20 000 l bioreactor according to the invention is preferably at least 85 and at most 115, more preferably the orifice- or pore-number is 100. The sparger length ($S_L$) for the control and/or the ballast sparger is preferably at least 500 mm and at most 2000 mm, more preferably the sparger length is 1077 mm. The sparger to tank bottom clearance ($S_c$) of the 20 000 l bioreactor according to the invention is preferably for the control and/or the ballast sparger at least 560 mm and at most 620 mm, more preferably the sparger to tank bottom clearance is 593 mm. The sparger to bottom impeller clearance ($D_c$–$S_c$) of the 20 000 l bioreactor according to the invention is for the control and/or the ballast sparger preferably at least 300 mm and at most 340 mm, more preferably the sparger to bottom impeller clearance is 320 mm. The requirement to add ballast from a separate sparger, the ballast sparger, prevents dilution of oxygen or oxygen enriched DOT demand gas with the ballast gas. This ensures the best oxygen transfer rate (OTR), as the oxygen concentration gradient of the bubbles emerging from the sparger is greatest. Secondly, the use of a ballast sparger allows spargers to be located at different positions to avoid impacting DOT control on delivering desired ballast for $pCO_2$ control. The ballast sparger can be independently designed from the control sparger.

With the bioreactor design according to the invention, different subculture ratios can be performed. In a particularly preferred embodiment the subculture ratios performed are subculture ratios of at least 1 in 5 (20% v/v) and at most 1 in 9 (11% v/v), more preferred 1 in 5 (20% v/v) or 1 in 9 (11% v/v).

The invention also includes a method to cultivate and propagate mammalian cells, characterised in that at least one mammalian cell is cultivated under suitable conditions and in a suitable culture medium in a bioreactor according the invention.

Bioreactors according to the invention include all bioreactors having at least two impellers and showing at least one feature or a combination of different features outlined above.

In the method according to the invention, the agitation rate of the at least two impellers of the bioreactor is preferably at least 55 $W/m^3$ and at most 85 $W/m^3$. Preferably, air is sparged into the culture medium with a speed of at least $5 \times 10^{-5}$ m/s, more preferably of at least $10 \times 10^{-5}$ m/s.

In a particularly preferred embodiment of the present invention alkali is added through two addition ports to distribute the alkali, which are, preferably spatially separated from each other. This ensures quicker blending of alkali in the event of long re-circulation time in the tank. $CO_2$ is preferably added via a control sparger.

Alkali and/or $CO_2$ are preferably used to regulate the pH of the culture-medium.

It is preferred that control and back-up probes be in the lower port ring at 913 mm from tank bottom.

In a preferred embodiment of the present invention, the method according to the invention takes place in a bioreactor with a volume of 1000 l. The volume of the culture medium used in the method using a 1000 l bioreactor is preferably during the pre-inoculation 50 l to 250 l. During the post-inoculation the volume of the culture medium is preferably at least 300 l and at most 960 l. In the pretransfer/harvest phase, the volume of the culture medium in the 1000 l bioreactor is preferably at least 300 l and at most 960 l. The minimum operating volume ($V_{min}$) in a bioreactor with the volume of 1000 l according to the invention is preferably between 80 l and 120 l, more preferably the minimum operating volume is 100 l, the maximum operating volume (V) is preferably at least 900 l and at most 1100 l, the maximum operating volume is more preferably 1000 l. The minimum stirred volume is preferably at least 230 l and at most 255 l, more preferably the minimum stirred volume is 245 l. The liquid height at the minimum operating volume ($H_{min}$) is in a bioreactor with a volume of 1000 l preferably at least 210 mm and at most 240 mm, more preferably the liquid height at the minimum operating volume is 228 mm. The liquid height at the maximum operating volume ($H_L$) in a bioreactor with a volume of 1000 l is preferably at least 1500 mm and at most 1900 mm, more preferably the liquid height at the maximum operating volume is 1764 mm. The minimum aspect ratio ($H_{min}/T$) is preferably at least 0.15 and at most 0.19, more preferably the minimum aspect ration is 0.17. The maximum aspect ratio ($H_L$-T) for the bioreactor with a volume of 1000 l used in a method according to the invention is preferably at least 1.8 and at most 2.1, more preferably the maximum aspect ratio is 1.96. The freeboard volume is preferably at least 270 l and at most 310 l, more preferably the freeboard volume is 293 l. The freeboard height is preferably at least 450 mm and at most 550 mm, more preferably the freeboard height is 500 mm. The total straight height (H) is preferably at least 1900 mm and at most 2200 mm, more preferably the total straight height is 2045 mm. The height of the upper probe- or sample-ring is preferably at least 900 mm and at most 1200 mm, more preferably the height of the upper probe- or sample-ring is 1093 mm. The height of the lower probe-sample ring is preferably at least 152 mm and at most 286 mm.

In a preferred embodiment of the present invention, the method according to the invention takes place in a bioreactor with a volume of 4000 l. The volume of the culture medium used in the method using a 4000 l bioreactor is preferably during the pre-inoculation 1914 l to 3077 l. During the post-inoculation the volume of the culture medium is preferably at least 2153 l and at most 3846 l. In the pretransfer/harvest phase, the volume of the culture medium in the 4000 l bioreactor is preferably at least 2153 l and at most 3846 l. The minimum operating volume ($V_{min}$) in a bioreactor with the volume of 4000 l according to the invention is preferably between 1500 l and 2200 l, more preferably the minimum operating volume is 1900 l, the maximum operating volume (V) is preferably at least 3800 l and at most 4200 l, the maximum operating volume is more preferably 4000 l. The minimum stirred volume is preferably at least 1500 l and at most 1800 l, more preferably the minimum stirred volume is 1654 l. The liquid height at the minimum operating volume ($H_{min}$) is in a bioreactor with a volume of 4000 l preferably at least 800 mm and at most 1200 mm, more preferably the liquid height at the minimum operating volume is 1024 mm. The liquid height at the maximum operating volume ($H_L$) in a bioreactor with a volume of 4000 l is preferably at least 1800 mm and at most 2200 mm, more preferably the liquid height at the maximum operating volume is 2034 mm. The minimum aspect ratio ($H_{min}/T$) is preferably at least 0.55 and at most 0.75, more preferably the minimum aspect ration is 0.63. The maximum aspect ratio ($H_L$-T) for the bioreactor with a volume of 4000 l used in a method according to the invention is preferably at least 1.1 and at most 1.4, more preferably the maximum aspect ratio is 1.25. The freeboard volume is preferably at least 850 l and at most 1250 l, more preferably the freeboard volume is 1039 l. The freeboard height is preferably at least 450 mm and at most 550 mm, more preferably the freeboard height is 500 mm. The total straight height (H) is preferably at least 2000 mm and at most 2400 mm, more preferably the total straight height is 2252 mm. The height of the upper probe- or sample-ring is preferably at least 1200 mm and at most 1600 mm, more preferably the height of the upper probe- or sample-ring is 1403 mm. The height of the lower probe- or sample-ring is preferably at least 500 mm and at most 550 mm, more preferably the height of the lower probe- or sample-ring is 531 mm.

In a preferred embodiment of the present invention, the method according to the invention takes place in a bioreactor with a volume of 20 000 l. The volume of the culture medium used in the method using a 20 000 l bioreactor is preferably during the pre-inoculation 13 913 l to 17 096 l. During the post-inoculation the volume of the culture medium is preferably at least 17 391 l and at most 19 231 l. In the pretransfer/harvest phase, the volume of the culture medium in the 20 000 l bioreactor is preferably at least 20 000 l and at most 21 739 l. The minimum operating volume ($V_{min}$) in a bioreactor with the volume of 20 000 l according to the invention is preferably between 9000 l and 16 000 l, more preferably the minimum operating volume is 13 000 l, the maximum operating volume (V) is preferably at least 19 000 l and at most 25 000 l, the maximum operating volume is more preferably 22 000 l. The minimum stirred volume is preferably at least 8100 l and at most 8500 l, more preferably the minimum stirred volume is 8379 l. The liquid height at the minimum operating volume ($H_{min}$) is in a bioreactor with a volume of 20 000 l preferably at least 2100 mm and at most 2500 mm, more preferably the liquid height at the minimum operating volume is 2309 mm. The liquid height at the maximum operating volume ($H_L$) in a bioreactor with a volume of 20 000 l is preferably at least 3550 mm and at most 3950 mm, more preferably the liquid height at the maximum operating volume is 3777 mm. The minimum aspect ratio ($H_{min}/T$) is preferably at least 0.70 and at most 0.99, more preferably the minimum aspect ration is 0.83. The maximum aspect ratio ($H_L$-T) for the bioreactor with a volume of 20 000 l used in a method according to the invention is preferably at least 1.2 and at most 1.5, more preferably the maximum aspect ratio is 1.35. The freeboard volume is preferably at least 5750 l and at most 6500 l, more preferably the freeboard volume is 6131 l. The freeboard height is preferably at least 900 mm and at most 1100 mm, more preferably the freeboard height is 1000 mm. The total straight height (H) is preferably at least 3700 mm and at most 4100 mm, more preferably the total straight height is 3968 mm. The height of the upper probe- or sample-ring is preferably at least 2200 mm and at most 2650 mm, more preferably the height of the upper probe- or sample-ring is 2411 mm. The height of the lower probe- or sample-ring is preferably at least 880 mm and at most 940 mm, more preferably the height of the lower probe- or sample-ring is 913 mm.

For a bioreactor with a volume of 20 000 l the preferred seeding ratio used is 11% v/v (1 in 9 dilution) or 20% v/v (1 in 5 dilution), with a preferred feed application of 4% v/v to 25% v/v of the post-inoculation volume. The post-inoculation volume in the 20 000 l bioreactor is preferably adjusted for feed applications up to 15% such that after the addition of all the feeds the final volume at harvest ends up at 20 000 l. However, for feed applications greater then 15% v/v the post-inoculation volume is preferably adjusted for a 15% v/v feed but following the application of feeds the final pre-harvest volume will be a minimum of 20 000 l and a maximum 22 000 l. The 20 000 l bioreactor is expected to hold a total of 20 000 l to 22 000 l at the end of a batch.

The bioreactor with a volume of 20 000 l is preferably operated in batch or fed batch mode for 10 to 15 days.

The invention also includes a bioreactor system for the cultivation of mammalian cells characterised in that a) a first bioreactor with a volume of at least 500 l, preferably of at least 1000 l, is connected with b) a second bioreactor with a volume of at least 2000 l, preferably of at least 4000 l, which has a volume greater than the first bioreactor and wherein the second bioreactor with a volume of at least 2000 l, preferably of at least 4000 l, is connected with c) a third bioreactor according to the invention having a volume of at least 10 000 l, preferably of at least 20 000 l, which has a volume greater than the second bioreactor.

In a preferred embodiment of the invention, the bioreactor system is characterised in that at least one of the bioreactors is a bioreactor according to the invention. More preferably, all of the bioreactors of the bioreactor system are bioreactors according to the invention.

Bioreactors according to the invention are in this context all bioreactors described in this description, in the examples and in the claims.

The bioreactor system according to the invention is also called bioreactor train or device.

The bioreactor train comprises preferably different bioreactors, which are also called stage. The bioreactor with a volume of at least 500 l, preferably of at least 1000 l corresponds to stage N-3 and/or N-2. The bioreactor with a volume of at least 2000 l, preferably of at least 4000 l corresponds to stage N-1. The bioreactor with a volume of at least 10 000 l, preferably of at least 20 000 l corresponds to stage N.

The design of the bioreactor train is based on the need to ensure a homogenous environment with respect to process parameters such as pH, dissolved oxygen tension (DOT) and temperature, maintaining a well mixed cell suspension and blending nutrient feeds within the bioreactor. The bioreactors of the bioreactor train preferably show geometric similarity. This allows a scale-down model to develop, for example at 12 l laboratory scales or 500 l pilot scales. The bioreactors of the stages N-3, N-2 and N-1 are used as seed-bioreactors. Bioreactor of stage N is used as a production-bioreactor. The design of the seed- and production-bioreactors is preferably based on the same principles. However, some departures can be required to allow for flexibility in processing.

In a preferred embodiment of the invention, the aspect ratio $H_L/T$ is at least 0.17 and at most 1.96.

In a preferred embodiment of the invention there is a further bioreactor, especially a 50 l bioreactor corresponding to stage N-4.

In a preferred embodiment of the invention, the N-4 bioreactor is a S-200 seed wave bioreactor or a 100 l stirred tank reactor In a preferred embodiment of the invention, liquids, for example culture medium, can be transported from one bioreactor to another bioreactor by pneumatic assisted flow or by peristaltic pumps.

The invention also includes a method to cultivate and propagate mammalian cells, characterised in that a) at least one mammalian cell is cultivated under suitable conditions and in a suitable culture medium in a first bioreactor with a volume of at least 500 l, preferably with a volume of at least 1000 l, b) the medium containing the cells obtained by propagation from the at least one mammalian cell is transferred into a second bioreactor with a volume of at least 2000 l, preferably with a volume of at least 4000 l, c) the transferred cells are cultivated in the second bioreactor with a volume of at least 2000 l, preferably with a volume of at least 4000 l, d) the medium containing the cells obtained in step c) is transferred into a third bioreactor with a volume of at least 10 000 l, preferably with a volume of at least 20 000 l, and e) the transferred cells are cultivated in the third bioreactor with a volume of at least 10 000 l, preferably with a volume of at least 20 000 l.

In a preferred embodiment of the invention, the method is characterised in that at least one of the bioreactors used is a bioreactor according to the invention, more preferably all bioreactors used are bioreactors according to the invention.

Bioreactors according to the invention are in this context all bioreactors described in this description, in the examples and in the claims.

The bioreactor of step e) is preferably operated in batch or fed batch mode. The cells are cultivated in step e) preferably for 10 to 15 days.

Step a) is also called stage N-3 and/or N-2. Step c) is also called stage N-1. Step e) is also called stage N.

Preferably the cultivation conditions in the bioreactors of steps a), c) and e) are the same. More preferably, the cultivation conditions in the bioreactors of steps a), c) and e) have a homogenous environment with respect to process parameters such as pH, dissolved oxygen tension and temperature. Preferably pH, dissolved oxygen tension and temperature in the bioreactors of steps a), c) and e) are the same.

In a preferred embodiment of the invention, the seeding ratio after the transfer steps b) and/or d) is at least 10% v/v, more preferably at least 11% v/v (1 in 9 dilution) and at most 30% v/v, more preferably 20% v/v (1 in 5 dilution).

Preferably either the total medium or only a part of the medium are transferred in steps b) and d).

Further preferred embodiments of the present invention are the subject-matter of the sub claims.

The present invention is illustrated in more detail in the following examples and the accompanying figures.

BRIEF DESCRIPTION OF THE FIGURES

FIG. 2 shows a bioreactor system of the present invention. 111 is a bioreactor with a volume of 1000 l. 11 is a bioreactor with a volume of 4000 l. 1 is a bioreactor according to the invention with a volume of 20 000 l.

EXAMPLES

Example 1

20 000 l Bioreactor

Figure 1:
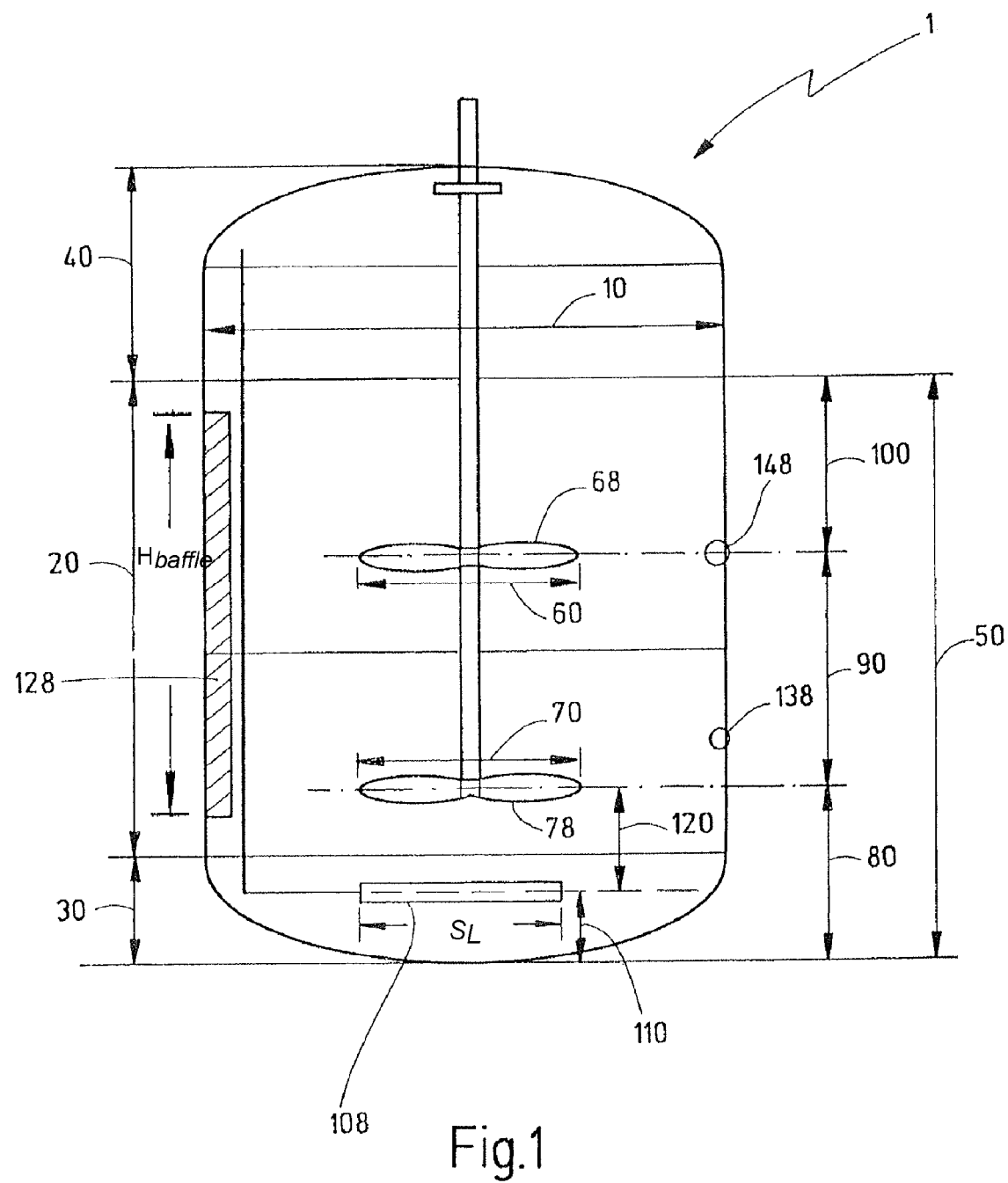
FIG. 1 shows a bioreactor according to the invention. 1 is the bioreactor. 10 is the diameter of the tank (T). 20 is the total straight height of the bioreactor (H). 30 is the base height of the bioreactor ($H_b$). 40 is the head height of the bioreactor ($H_h$). 50 is the liquid height at the maximum operating volume ($H_L$). 60 is the top impeller diameter ($D_{top}$). 68 is the top impeller. 70 is the bottom impeller diameter ($D_{bottom}$). 78 is the bottom impeller. 80 is the clearance between tank bottom and centre line of the bottom impeller ($D_c$). 90 is the impeller separation ($D_s$). 100 is the clearance of the top impeller below the liquid surface ($D_c$). 108 is a sparger. 110 is the sparger to tank bottom clearance ($S_c$). 120 is the sparger to bottom impeller clearance ($D_c$–$S_c$). 128 is a baffle. 138 is a port located at the lower ring. 148 is a port located at the centre-line of the top impeller 68.

The 20 000 l bioreactor is operated in batch and fed batch mode for 10 to 15 days for the cultivation of mammalian cells. The mammalian cells are kept in a homogeneous suspension by agitation via an impeller system.

Vessel Geometry

The vessel geometry for the 20 000 liter bioreactor was determined by an iterative design basis in which the maximum working volume, freeboard straight side distance, aspect ratio $H_L/T$ and impeller to tank diameter, $D/T$ ratio are altered until an acceptable aspect ratio is achieved.

Bioreactor Aspect Ratio $H_L/T$

This critical design parameter allows characterisation of bioreactor geometry. Tanks with higher aspect ratio offer longer gas residence time allowing greater $K_La$. However increased head pressure can cause build up of soluble gases. Smaller aspect ratio $H_L/T$ in tanks can lead to shorter gas residence time requiring greater gas flow for aeration resulting in greater foam build up. Impeller driven agitation to increase $K_La$ is also limited by $H_L/T$ as surface breakage and vortex creation will occur at lower impeller revolutions in a low aspect ratio. Thus choice of aspect ratio is largely experience based with some thought on issues highlighted in table 1.

TABLE 1

Summary of effect of varying aspect ratio

| Process factor | High aspect ratio | Low aspect ratio |
| --- | --- | --- |
| Radial mixing | More effective | Less effective |
| Mixing time | Higher | Lower |
| Oxygen transfer rate | Determined by dissolved oxygen control | Determined by dissolved oxygen control |
| Gas flow rate | Lower | Higher |
| Cell damage | Less | More |
| Carbon dioxide stripping | Less effective | More effective |
| Pressure variations | Higher | Lower |
| Ease of scale up/scale down (access to scale data) | More difficult away from currently used aspect ratios | More difficult away from currently used aspect ratios |
| Cleanability | Not affected directly by aspect ratio | Not affected directly by aspect ratio |
| Volume flexibility | Less | More |

Table 2 describes the aspect ratios in the 20 000 liter bioreactor at various operating volumes during normal processing. The aspect ratios have been tested at 500 liter scale and provided the superficial gas velocity and power per unit volume are kept constant the $K_La$ remains constant.

TABLE 2

Key operating volumes and aspect ratios in the 20000 litre bioreactor

| | Volume, L | Liquid head, mm | Aspect ratio, $H_L/T$ |
| --- | --- | --- | --- |
| Pre-Inoculation | 13913-17096 | 2458-2977 | 0.88-1.07 |
| Post Inoculation | 17391-19231 | 3025-3325 | 1.08-1.19 |
| Harvest | 20000-21739 | 3451-3734 | 1.23-1.34 |

Tank Diameter

The tank diameter is altered to obtain the optimal aspect ratio $H_L/T$. Changes to tank internal diameter (ID) are limited by acceptable aspect ratio and plant footprint. The ID is 2.794 m.

Tank Height

Tank height is determined from the maximum operating volume, aspect ratio $H_L/T$, freeboard straight side length, base and top plate design. The final tank height is a compromise value determined from volumetric contingency for foam, plant height and impeller shaft length. The tank height from base to head tan line is 4.933 m.

Freeboard Height

The freeboard height is defined as the length of straight side above the liquid head when the bioreactor is filled to it's maximum operating volume. This is determined by taking into account the extent of:

Foam build up during operation.
Gas hold up at maximum allowed agitation and aeration.
Errors in metering liquid.

In absence of knowing the exact contribution of each with piloting the process at full scale an estimate is usually made. The amount of freeboard height is balanced with the desire to reduce the impeller shaft length for a top-driven system, where extra length can complicate the design and selection of available mechanical seals, the requirement for steady bearing or stabilising impeller rings. A minimum freeboard height of 1000 mm (or 6100 liter volumetric capacity or 28% v/v of the maximum operating volume) is therefore used.

Head and Base Plate

The selection of head and base plate design was made with a consideration for desired mechanical strength, free draining clean design and fluid flow. Maintaining consistent plate design between scale down and full scale will contribute towards maintaining geometric similarity. The base plate is of American Society of Mechanical Engineers Flanged and Dished (ASME F&D) design. The head-plate design accommodates a manway or a flanged head plate to allow access/removal of the impellers.

Bioreactor Agitation Requirement

The agitation of the bioreactor is to achieve rapid mixing, maintain homogeneity, maintain mammalian cells in suspension and gas bubble dispersion. The underlying issue with achieving the above objectives is minimising cell damage through shear forces originating from impeller geometry and eddies or vortices created behind the impeller blades. A compromise of the above objectives can be achieved by selection of an appropriate impeller type.

Bottom Versus Top Driven Impeller Shaft

The decision to drive the agitator shaft from the top or the bottom of the bioreactor is important and is determined following a review of a number of issues highlighted in table 3.

TABLE 3

Key design issues for selection of top versus bottom entry of impeller shaft

| | Top entry | Bottom entry |
| --- | --- | --- |
| Shaft Length | Long | Short |
| Shaft Weight | High | Low |
| Shaft Diameter | Larger | Smaller |
| Impeller shaft on-site installation and removal for servicing and repair | Greater plant height | Less plant height |
| Exposure of cell culture to moving and stationary seal faces | No exposure | Exposure |

TABLE 3-continued

Key design issues for selection of top versus bottom entry of impeller shaft

| | Top entry | Bottom entry |
|---|---|---|
| [1]Pressurization between seal and vessel | Lower | Higher due to the liquid head |
| Seal Lubricant leakage rate | Lower | Higher |
| Base plate Design | Simple | Complex |
| Sparger to tank bottom positioning | Unrestricted | Restricted |
| CIP validation | Simple | Complicated by sub-merged mechanical seal |
| Scale up and scale down consistency | Consistent with lab and pilot scale | Inconsistent with lab and pilot scale |

[1]Pressure differential between seal and bioreactor critical for lubrication and cooling.

Top-entry impeller shafts tend to be longer than bottom-entry, which results in the shaft being heavier and larger diameter. Additionally the shaft length together with the inherent clearance between the two faces of the mechanical seal may dictate the requirement for steady bearings or stabilising ring to prevent excessive "shaft wobble". Service and maintenance are affected by the available space around the agitator, gearbox and seal assembly, and on-site shaft installation and removal is limited by plant height.

The protrusion of the seal and impeller shaft at tank bottom restricts the placement of the sparger near the tank bottom. This dimension affects the tank hydrodynamics and therefore its amenability to change is important in specifying an optimal design.

The downwards load of down pumping impellers together with the liquid head have an accumulative greater load (compared to up pumping or top-entry shaft) between the moving and stationary faces of the seal resulting in greater wear of the seal faces. Furthermore loss of over pressure in the condensate line supplying the seal can result in the culture seeping into the seal. This makes the subsurface seal a less sanitary design.

The submerged seal complicates the design of a free draining bioreactor by compromising the position of the harvest drain valve. Secondly the diameter of the harvest nozzle may be restricted thus restricting the flow rate of harvest stream. Therefore a top entry impeller shaft is used in the 20 000 liter bioreactor.

Baffles

The baffle requirement for centre mounted impeller is critical to prevent vortex formation. The critical issues related to baffles are baffle number, baffle width (W), baffle length ($H_{baffle}$) and baffle to tank wall clearance ($W_c$).

The recommendation for four equally spaced baffles that are 0.1×T or 279 mm wide 1.1×H–$H_h$ or 3882 mm tall and have a baffle to tank wall clearance, $W_c$ of 0.01×T or 28 mm.

The thickness of baffle is not specified but the thickness needs to ensure rigidity to the radial component of the fluid flow. Additionally thickness needs to ensure the baffle plates are not warped during SIP thereby affecting the baffle to tank wall clearance.

Impeller Type

High shear, such as Rushton (or Rushton-type), impellers offer high power dissipation for gas dispersion but lack in axial flow necessary for mixing and homogeneity. Additionally, agitation from high shear impellers suffers from dangers of excessive cell damage.

Table 4 shows the impellers tested at lab scale (12.2 liter) that gave equivalent hydrodynamic and cell growth performance. The hydrofoil is mounted above the high solidity pitched blade impeller.

The Lightnin A310 and A315 at the D/T ratio described in table 4 are used in the bioreactor.

TABLE 4

Impeller types short-listed for scale down study

| Impellers | D/T ratio | [1]$N_p$/[2]$N_q$ | Vendor | Description |
|---|---|---|---|---|
| A310 | 0.44 | 0.30/0.56 | Lightnin | Three bladed hydrofoil design |
| A315 | 0.46 | 0.75/0.73 | Lightnin | Four pitched-bladed high solidity impeller |
| SC-3 | 0.40 | 0.90/0.90 | Chemineer | Three bladed hydrofoil design |
| 3HS39 | 0.46 | 0.53/0.58 | Philadelphia Mixers | Four pitched-bladed high solidity impeller |

[1]$N_p$ is characteristic impeller power number. It is a measure of an impeller efficiency to impart the kinetic energy of the rotating impeller blades to the fluid. It is important in quantifying the gas dispersion
[2]$N_q$ is characteristic impeller flow number. It is a measure of pumping ability of the impeller and is important in quantifying fluid bulk movement.

Impeller to Tank Diameter, D/T Ratio

The diameter for axial flow impellers is recommended to be less than 0.5×T. A diameter greater than this results in disruption in axial flow, hence poor agitation and aeration.

Power dissipation into the bioreactor and Reynold's number also need to be sufficiently high to maintain a turbulent (loaded) regime. Therefore the selection of impeller diameter is a compromise between choosing large enough diameter to ensure adequate homogeneous mixing without exceeding the hydrodynamic characteristics of the bioreactor. These include throttling axial flow, insufficient power dissipation, exceeding upper limits of impeller tip speed and creation of poorly mixed laminar zone.

Once a diameter is selected, than maintaining constant D/T ratio is critical between scale down pilot vessels in order to maintain the central assumption of scale studies—that of maintaining geometric similarity.

The $K_La$ scale up correlation at 12.2 liter has been determined for the four impellers at the D/T ratios shown in table 4. From a geometric similarity standpoint A310 diameter of 1.229 m (D/T of 0.44) and A315 diameter of 1.285 m (D/T of 0.46) is recommended. However a manway diameter can restrict the largest impeller diameter that can be installed and removed to 1.219 m. Therefore A310 and A315 to be 1.219 m diameter are used thereby keeping with ease of impeller installation and removal and maintaining close to the geometric similarity proposed in scale down study.

The Impeller Clearance, $D_c$ and Spacing, $D_s$

The spacing between impellers in a bioreactor with multiple impellers is an important dimension to consider. For a bioreactor with dual Rushton turbine (radial flow) the ungassed power consumption is equivalent to a single impeller when the dual impeller are spaced less then 0.5×D along the shaft. At a spacing of 2×D the power consumption becomes adductive. Thus efficiency of the impeller is reduced when the impeller spacing becomes less then 0.5×D and the requirement for multiple impellers becomes unnecessary. It is important to note that impeller spacing also impacts on the potential of creating dead zones (poorly mixed zones) within the bioreactor. An additional constraint on the choice of impeller spacing is discrete working volumes required within the bioreactor.

The impeller spacing, $D_s$, of $1.229 \times D_{bottom}$ (1498 mm) allows both impellers to remain submerged at the lowest post-inoculation volume of 17392 liters with liquid head above the upper impeller, $D_o$, of $0.5 \times D_{top}$ (615 mm) and off bottom clearance, $D_C$, of $0.75 \times D_{bottom}$ (913 mm).

Table 5 highlights volumes that will form liquid surfaces or lower liquid cover, above the impellers. Agitation needs to be modified to avoid foaming at these critical volumes.

TABLE 5

Key operating volumes that cause interaction with impellers and liquid surface

| Interaction | Volume, L | Potential Operation |
|---|---|---|
| Submerge top impeller with $0.5D_{A310}$ liquid cover | 17399 | Minimum post inoculation volume 17391 L |
| Liquid surface touching top edge of top impeller | 13973 | Pre-inoculation volume of 13913 L liquid surface breakage |
| Liquid surface touching bottom edge of top impeller | 13283 | Bolus addition of pre-inoculation medium will pass through this liquid head |
| Submerge bottom impeller with $0.5D_{A315}$ liquid cover | 8381 | Bolus addition of pre-inoculation medium will pass through this liquid head |
| Liquid surface touching top edge of bottom impeller | 5592 | Bolus addition of pre-inoculation medium will pass through this liquid head |
| Liquid surface touching bottom edge of bottom impeller | 3291 | Bolus addition of pre-inoculation medium will pass through this liquid head |

[1]Minimum operating volume with lower impeller submerged is 8379 litres and minimum operating volume with both impellers submerged is 17399 litres
[2]The operating volume range is 13913 to 21739 litres.

Clearance of Top Impeller Below Liquid Surface, Do.

The breakage of the impeller blade above liquid surface is undesirable as this will make the flow and power dissipation of the impeller ineffective. In addition it will create unknown $K_La$ values due to significant surface entrapment of headspace gas into the fluid and excessive foam. $D_o$ is 0.3×D for radial flow impellers and 0.5×D for axial flow impellers such as A310. However as $D_o$ approaches 2×D the impeller provides gentle blending duty. This is acceptable for the production bioreactor application as $K_La$ study has shown that bioreactor $K_La$ is influenced mostly by the bottom A315 impeller and the top A310 impeller contributes to bulk mixing.

As a result of setting $D_c$ and $D_s$ at values $D_o$ is maintained at an optimal range for the duration of operation of the production bioreactor. During the course of a batch the liquid cover above the top impeller will change from $0.5 \times D_{A310}$ and $1.08 \times D_{A310}$. The liquid cover above the top impeller will increase as the bioreactor is fed nutrient feeds and alkali to maintain constant pH. Table 6 shows a range of liquid cover above the top impeller for a range of operating volumes.

TABLE 6

Key operating volumes and the liquid cover above top impeller, Do

| Operating volume, L | Cylinderical height, H mm (inches) | Do, mm (inches) | Do as ratio of $D_{A310}$ |
|---|---|---|---|
| Pre-Harvest, 21739 L | 3252 (128") | 1324 (52") | $1.08D_{A310}$ |
| Pre-Harvest, 20000 L | 2968 (117") | 1040 (41") | $0.85D_{A310}$ |
| Post-Inoculation, 19231 L | 2843 (112") | 915 (36") | $0.74D_{A310}$ |
| Post-Inoculation, 17391 L | 2543 (100") | 615 (24") | $0.5D_{A310}$ |
| Pre-Inoculation, 15385 L | 2215 (87") | 287 (11") | $0.23D_{A310}$ |
| Pre-Inoculation, 13913 L | 1973 (78") | 45 (2") | $0.04D_{A310}$ |

[1]Off bottom impeller clearance, Dc = 913 mm ($0.75D_{A315}$), Impeller separation, Ds = 1498 mm ($1.229D_{A315}$), tank ID of 2794 mm and height of ASME F&D base plate, $H_h$ = 483 mm
[2]$D_o = H - D_s - (D_c - H_h)$ Agitation Rate—Rpm, P/V and Tip Speed Table 7 below specifies the agitation rate for the 20 000 liter bioreactor. The bioreactor is agitated typically at 20-260 W/m³, preferably at 55-85 100 W/m³. The agitation strategy is being developed during the 500 liter pilot fermentations. The agitation rate of 0 to 80±1 rpm is therefore used as an operational range.

TABLE 7

Agitation rate for the 20000 L bioreactor

| | Agitation rate, rpm | Power per unit volume, W · m⁻³ | Tip Speed, m/s |
|---|---|---|---|
| Pre-inoculation | Typically 28-30 can be be higher | Typically 20 can higher | 1.8-1.9 |
| Post-inoculation until harvest | Typically 56 can be up to 80 | Typically 103, can be up to 260 | 3.6 can be up to 5.1 |

Mechanical Seals Specification

For bioreactor all seals are to be double mechanical seals with a maximum "run out" or wobble tolerance of 0.2 mm. Three types were considered; these include:
  Wet seal lubricated with sterile condensate.
  Dry seal lubricated with sterile gas such as $N_2$ or CA.
  Non lubricated or floating seal that are uni-rotational.
All mechanical seals are recommended to be serviced on an annual basis. This requires the removal of seal from the bioreactor and sending the seal assembly to the vendor. Therefore the design must consider ease of routine maintenance.

The dry type seal (John Crane—5280D type) will produce 3 g per year of shedding (seal face and seal seat material) composed of resin impregnated carbon. This is based on continuous 24 hour operation over a year. The amount of shedding for the wet seal is significantly less. Therefore a wet condensate-lubricated seal is adopted for all bioreactor double seals.

Bioreactor Aeration Requirement and Gassing Strategy

The aeration duty of the 20 000 liter bioreactor is governed by:
  $K_La$ requirement.
  DOT control strategy.
  $pCO_2$ control/stripping strategy.
  Use of sintered or fluted spargers.

The 20 000 liter bioreactor is designed to provide $K_La$ values of up to 20 h⁻¹ for processes with oxygen uptake rates of 5 mmol×L⁻¹×h⁻¹. The bioreactor design needs to be flexible enough to allow cultivation of processes reaching 20×10⁶ cells×mL⁻¹.

The aeration requirement can be achieved by a number of different approaches. However the use of a fluted sparger with air and oxygen enrichment to make up any deficit in oxygen transfer rate (OTR) during peak oxygen demand was used. The advantages of this approach are:

Easier CIP and SIP validation of fluted sparge design.
Larger air throughput to aid dissolved $CO_2$ stripping.
Reduced operating cost through the avoidance of purchase of single use sintered elements.

The disadvantages of the approach selected above also need to be considered. These include:

Inherent lower $K_La$ for the low power number impellers selected.

Therefore the bioreactor aeration design must have the flexibility to be modified to meet the desired $K_La$.

Table 8 describes the gassing requirements for the 20 000 liter bioreactor. The gas flow rates were scaled up on constant superficial gas velocity.

Two spargers are used. The main or "DOT control" sparger supplied by dual range clean air, mass flow controller (MFC) and oxygen MFC with gas flow metered via a DOT control loop and a $CO_2$ MFC metering gas via the acid pH control loop. The dual range MFC's are used to achieve precise flow control at the extreme ends of the desired operating ranges.

The second or "ballast" sparger is supplied by a CA MFC to which nitrogen is also supplied. It was measured that early DOT control requires small nitrogen ballast to assist in early DOT demand and lower the DOT to set point. The ballast sparger also meters ballast air to facilitate stripping out excess $pCO_2$.

The headspace purge is used to allow removal of $CO_2$ and oxygen from the headspace. This is to facilitate better pH and $pCO_2$ control and dilution of high oxygen blend prior to exhausting to environment. The ability to vary headspace flow rate allows design of gassing strategy for various processes requiring different blends of oxygen enrichment and control point $pCO_2$.

TABLE 8

Gas flow rate and MFC operating ranges for the 20000 litre bioreactor

| Gas | Operating range | Comments |
|---|---|---|
| Head Space[1] | | |
| 1.) Clean air | 1.) 0-1000 SLPM | 1.) Head space purging of $CO_2$ and $O_2$ |
| 2.) Nitrogen | 2.) Utility rated | 2.) For rapid DOT probe zeroing |
| 3.) Helium | 3.) Utility rated | 3.) Tank integrity testing |
| DOT control Sparger | | |
| 1.) Clean air[2] | 1.) 10-500 SLPM | 1.) Gas flow under DOT control |
| 2.) Oxygen | 2.) 10-100 SLPM | 2.) Gas flow under DOT control |
| Carbon dioxide[3] | 3.) 2-150 SLPM | 3.) Gas flow under pH control |
| Ballast Sparger | | |
| 1.) Clean air | 1.) 20-500 SLPM | 1.) Variable ballast for $dCO_2$ stripping |
| 2.) Nitrogen[4] | 2.) 20-500 SLPM | 2.) Early DOT control by variable flow |

[1]The air and nitrogen gas flow into headspace enters via a bypass for post SIP tank pressurisation.
[2]Clean air gas flow operating range achieved by a dual CA MFC at 5-50SLPM and 50-500SLPM respectively.
[3]$CO_2$ gas flow operating range achieved by a dual $CO_2$ MFC at 2-30SLPM and 30-150SLPM respectively.
[4]Both air and nitrogen gas flow metered from a common CA MFC.

The bioreactor ports for sparger installation are designed to fit pipe design of diameter of 51 mm. The position of port should allow the placement of control sparger ($D_c$-$S_c$) at a distance of 320 mm below the bottom edge of the lower impeller and no greater 593 mm from tank bottom ($S_c$).

This results in a $S_c$ value of 593 mm or (0.65×$D_c$) and this falls outside the acceptable range of 0.2×Dc to 0.6×Dc. However hydrodynamic trials in 500 l suggest $S_c$ clearance of 0.41 to 0.71×$D_c$ has no impact on measured $K_La$.

A separate port for the installation of the ballast sparger was also built. The position of this port allows the placement of ballast sparger at a distance of 320 mm, ($D_c$-$S_c$) below the bottom edge of the lower impeller and no greater then 593 mm from tank bottom ($S_c$). The requirement to add ballast from a separate sparger is due to three reasons:

Firstly, it prevents dilution of oxygen or oxygen enriched DOT demand gas with the ballast gas. This ensures the best OTR, as the oxygen concentration gradient of the bubbles emerging from the sparger is greatest.
Secondly, it allows ballast sparger to be located at a different position from DOT control sparger to avoid impacting DOT control on delivering desired ballast for $pCO_2$ control.
Thirdly, the ballast sparger can be independently designed from the DOT control sparger.

The calculation of hole size and number of holes is iterated until the target Reynold's number, Re of gas emerging from holes is <2000 and the Sauter mean diameter for a bubble is 10-20 mm during chain bubble regime. Table 9 shows the key specifications for the control and ballast sparger for the 20 000 liter bioreactor.

TABLE 9

Design specification for the 20 000 litre bioreactor spargers

| Parameter | DOT control sparger | Ballast sparger |
|---|---|---|
| Gas flow, SLPM | 850 | 500 |
| Number of sparge holes | 250 | 100 |
| Orifice diameter, $d_o$, m | 0.004 | 0.006 |
| Gas flow, $m^3 \cdot s^{-1}$ | 1.42E-02 | 8.33E-03 |
| Orifice area, $m^2$ | 1.26E-05 | 2.83E-05 |
| Total orifice area, $m^2$ | 3.14E-03 | 2.83E-03 |
| Density of air, $Kg \cdot m^{-3}$ | 1.166 | 1.166 |
| Viscosity, $Nm \cdot s^{-2}$ | 1.85E-05 | 1.85E-05 |
| Sauter mean diameter, $d_{vs}$, mm ($d_{vs} = 1.17\, V_o^{0.4}\, d_o^{0.8}\, g^{-0.2}$) | 16.34 | 19.06 |
| Gravitational acceleration, $g\, m \cdot s^{-2}$ | 9.807 | 9.807 |
| Density difference, $Kg \cdot m^{-3}$ | 1048.834 | 1048.834 |
| Reynold's number, >2000 jetting regime | 1139 | 1117 |
| Gas velocity at sparger, $V_o$, m/s | 4.51 | 2.95 |
| Sparger length, $S_L$, m | 1.077 | 1.077 |
| Combined length to drill required holes, m | 1.000 | 0.6 |
| Number of rows to fit required holes in length $S_L$ | 2 | 1 |
| Sparger to tank bottom clearance, Sc, m | 0.593 | 0.593 |
| Sparger to bottom impeller clearance, Dc-Sc, m | 0.320 | 0.320 |

A ring sparger of 0.8×$D_{bottom}$ (80% diameter of bottom A-315 impeller diameter) is used to distribute the holes under the blades and not the impeller hub. However the CIP and installation of this configuration is difficult. Therefore selection of sparger geometry that permits distribution of the desired number of holes in a manner that is consistent with best to distribute the holes and sanitary design can be used also.

As an option a crescent rather then straight pipe is explored. The curvature of the crescent is 0.8×$D_{bottom}$. In order to aid installation and removal from side ports of the bioreactor the crescent circumference is 240° of the complete circumference of $0.8 \times D_{bottom}$ ring, this is 1077 mm.

The DOT control sparger is 1077 mm long and has a 51 mm diameter. The holes have a 4 mm diameter. A total of 250 holes divided into 2 rows (2×125) at 45° from the dorsal (vertical) are used. Drain holes of 4 mm diameter on both ends of the sparger are drilled on the ventral side of the sparger to aid free CIP drainage of the sparger.

The ballast sparger is 1077 mm long and of 51 mm diameter and has a total of 100 6 mm diameter holes in a single dorsal row. Drain holes of 4 mm diameter on both ends of the sparger are drilled on the ventral side of the sparger to aid free CIP drainage of the sparger.

Position of Probes, Addition and Sample Ports

The probe ring position must be placed in a well-mixed representative region of the bioreactor. Additional considerations included working volume range and ergonomic operations. The location of probe ports, sample valve and addition points were considered together to avoid transitory spikes. Furthermore the position of the sample valve with respect to controlling probes needs to permit accurate estimation of off-line verification of the measured process parameter. This is shown in table 10.

TABLE 10

Probe, addition and sampling port specification for the 20000 litre bioreactor

| Probe/Port | Location | [2]Diameter, mm (inches) | [1]Position, mm (inches) | Rational |
|---|---|---|---|---|
| Temperature (main) | Lower ring | 38.1 (1.5") | 1.) 913 (36") 2.) 30° | In the plane of centre-line of bottom impeller |
| Temperature (backup) | Lower ring | 38.1 (1.5") | 1.) 913 (36") 2.) 170° | In the plane of centre-line of bottom impeller |
| pH (main) | Lower ring | 38.1 (1.5") | 1.) 913 (36") 2.) 10° | In the plane of centre-line of bottom impeller |
| pH (backup) | Lower ring | 38.1 (1.5") | 1.) 913 (36") 2.) 20° | In the plane of centre-line of bottom impeller |
| DOT (main) | Lower ring | 25.0 (0.98") | 1.) 913 (36") 2.) 150° | In the plane of centre-line of bottom impeller |
| DOT (backup) | Lower ring | 25.0 (0.98") | 1.) 913 (36") 2.) 160° | In the plane of centre-line of bottom impeller |
| pCO$_2$ (spare) | Lower ring | 50.8 (2")tbd | 1.) 913 (36") 2.) 20° | In the plane of centre-line of bottom impeller |
| Biomass (spare) | Lower ring | 50.8 (2") | 1.) 913 (36") 2.) 160° | In the plane of centre-line of bottom impeller |
| Spare probe port (DOT-type) | Lower ring | 25.0 (0.98") | 1.) 913 (36") 2.) 150° | In the plane of centre-line of bottom impeller |
| Spare probe port (pH-type) | Lower ring | 38.1 (1.5") | 1.) 913 (36") 2.) 10° | In the plane of centre-line of bottom impeller |
| Sample valve (main) | Lower ring | 12.7 (0.5") | 1.) 913 (36") 2.) 40° | NovAseptic type |
| Sample valve (backup) | Lower ring | 12.7 (0.5") | 1.) 913 (36") 2.) 50° | NovAseptic type |
| Alkali addition 1 - Tank 1 | Lower ring | 50.8 (2") | 1.) 913 (36") 2.) 190° | Diametrically opposite pH probes |
| Alkali addition 2 - Tank 1 | Centre-line of upper impeller | 50.8 (2") | 1.) 2411 (95") 2.) 190° | Diametrically opposite pH probes |
| Continuous feed 1 - Tank 2 | Lower ring | 50.8 (2") | 1.) 913 (36") 2.) 200° | Diametrically opposite pH probes |
| Continuous feed 2 - Tank 3 | Lower ring | 50.8 (2") | 1.) 913 (36") 2.) 210° | Diametrically opposite pH probes |
| DOT control sparger orifice | N/A | 101.6 (4") | 1.) 593 (23") 2.) 0° | Diametrically opposite ballast sparger |
| Ballast sparger orifice | N/A | 101.6 (4") | 1.) 593 (23") 2.) 180° | Diametrically opposite control sparger |
| Overlay gas | Head plate | 101.6 (4") | 1.) N/A 2.) 135° | Diametrically opposite vent out |
| Exhaust vent out | Impeller flange plate | 50.8 (2") | 1.) N/A 2.) 315° | Diametrically opposite overlay gas in |

TABLE 10-continued

Probe, addition and sampling port specification for the 20000 litre bioreactor

| Probe/Port | Location | [2]Diameter, mm (inches) | [1]Position, mm (inches) | Rational |
|---|---|---|---|---|
| Harvest valve | Base plate | 76.2 (3.0") | 1.) N/A<br>2.) Centre | NovAseptic type to allow free draining |
| Antifoam addition | Head plate | 50.8 (2") | 1.) N/A<br>2.) 170° | Liquid surface/ 0.25T from tank centre |
| Shot feed 1 - LS1 | Head plate | 50.8 (2") | 1.) N/A<br>2.) 190° | Liquid surface |
| Shot feed 2 - Glucose shot | Head plate | 50.8 (2") | 1.) N/A<br>2.) 180° | Liquid surface |
| Small add - Spare | Head plate | 50.8 (2") | 1.) N/A<br>2.) 200° | Liquid surface - directed into vessel wall |
| Media inlet | Head plate | 101.6 (4") | 1.) N/A<br>2.) 310° | Nozzle directed onto vessel wall |
| Inoculum transfer from 4000 L to 20000 L | Head plate | 101.6 (4") | 3.) N/A<br>4.) 320° | Nozzle directed onto vessel wall |
| CIP - Spray ball | Impeller flange plate | 76.2 (3") | 1.) N/A<br>2.) 270° | CIP'ing of highest point |
| CIP - Spray ball | Head plate | 76.2 (3") | 5.) N/A<br>6.) 60° | As per CIP design |
| CIP - Spray ball | Head plate | 76.2 (3") | 1.) N/A<br>2.) 180° | As per CIP design |
| CIP - Spray ball | Head plate | 76.2 (3") | 1.) N/A<br>2.) 300° | As per CIP design |
| Pressure indicating transmitter (PIT) | Head plate | 38.1 (1.5") | 1.) N/A<br>2.) 60° | As per vessel vendor design |
| Pressure gauge | Head plate | 38.1 (1.5") | 1.) N/A<br>2.) 50° | As per vessel vendor design |
| Rupture disc | Head plate | 101.6 (4") | 1.) N/A<br>2.) 280° | As per vessel vendor design |
| Spare nozzle | Head plate | 101.6 (4") | 1.) N/A<br>2.) 160° | As per vessel vendor design |
| Sight glass | Head plate | 101.6 (4") | 1.) N/A<br>2.) 70° | As per vessel vendor design |
| Light glass | Head plate | 76.2 (3") | 1.) N/A<br>2.) 75° | As per vessel vendor design |
| Manway | Head plate | 457.2 (18") | 1.) N/A<br>2.) 90° | Personnel entry |
| Agitator head/flange | Head plate | 1320.8 (52") | N/A | Entry/removal |
| Impeller shaft and seal manway | Agitator head/ flange | 304.8 (12") | N/A | Entry/removal |

[1]Measured from the tangential line of the base plate. Degrees pertain to plane of clockwise rotation.
[2]Diameter of nozzle at bioreactor.

Addition Ports, Surface and Sub-Surface

The need to determine addition ports that terminate at liquid surface and those that are subsurface was determined by operational scenarios and the effects of feed strategy on process control.

Currently the protein free process has two continuous feeds that need to be discharged in well-mixed area of the bioreactor. Additional provision for glucose and an "LS1-type" shot addition is also integrated in the well mixed region. The foam is controlled by surface addition of 1 in 10 diluted C-emulsion. The inoculation of seed into the pre-inoculation bioreactor is served by avoiding build up of foam which will arise as the culture is dropped onto the surface of the medium. Following ports were designed:

Six surface additions with media inlet, inoculum inlet, one small addition inlet directed into the wall of the vessel while the others dropped onto the liquid surface away from the tank wall.

Four subsurface additions comprised of inlets from the two feed tanks and bi-level inlet from the alkali tank.

Sample Ports

The sample port design allows a representative sample to be taken from the bioreactor. Therefore any residual material must be as small as possible. The samples taken are used to determine off line checks for dissolved gases, pH, nutrients and biomass concentration. The orifice of the port opening is large enough to prevent sieving causing biomass aggregates to be retained. The 2 mm orifice NovaSeptum sampling device was used. However this has to be balanced with the desire to keep residual volume of the port low. The port needs to be positioned in a well-mixed zone adjacent to the probes that need to be verified by off-line checks and will be determined via nozzle position (see table 10).

Add Tanks

In order to reduce cost and time the add-tanks supplying the bioreactor are of modular design. The production bioreactor has three 2500 liter nominal volumes add tanks. The add tanks are filled at 25 l/min. The flow rate of feeds from the add tanks to the bioreactor is controlled at 0.2 to 1.0 milliliters of feed per liter of post-inoculation bioreactor volume per hour (ml/l/h). It is expected that feed rate is controlled at ±5% of set point.

The production bioreactor is serviced by three 1372 mm ID by 1880 mm add tanks. These tanks have the capability to be cleaned and sterilised independently and together with the production bioreactor.

Manway

Access into the bioreactor is required for certain service operations. Access can be gained by considering a flanged head plate or incorporation of a manway into the head plate. The need for access into the bioreactor is for:
Installation of impellers.
Installation and replacing of impeller and impeller shaft.
Installation and replacing of mechanical seal.
Service of vessel furniture.
Potential modification of sparger position to obtain desired hydrodynamic characteristics.

The size of the manway must be sufficient to allow access for the above objectives. The manway used was of sufficient diameter to allow the removal of two impellers of 1219 mm diameter.

Volume Measurement

The design ensures that any sensor gives sufficient precision in volume measurement around the operating range.

The volume measurement in bioreactor is able to measure a range of 13 000 to 25 000 liters. The sensor sensitivity needs to be at least 0.5% of full span.

Volume measurement in the feed add-tanks and alkali tank is able to measure 0 to 2200 and 2500 liters respectively. The sensor sensitivity needs to be at least 0.2% of full span. This will permit hourly verification of feed flow rate at the minimum flow rate of 0.2 ml/l per hour or 3.5 l per hour by measuring the volume decrease in the add tanks.

Bioreactor Temperature Control

The medium is brought to operating temperature and pH by process control. This is achieved by "gentle" heating of the jacket (avoid high temperature at vessel wall). The temperature control range during operation is 36 to 38° C. with an accuracy of ±0.2° C. at set point.

Jacket

The bioreactor jacket area is specified with the following considerations in mind:—
Steam sterilisation at 121-125° C.
Warming up of medium from 10° C. to 36.5° C. in <2 h.
All points within the bioreactor must reach ±0.2° C. of set point, typically 36.5° C., as measured by thermocouples.
Chilling of medium from 36.5° C. to 10° C. in <2 h.

Bioreactor pH Control

The process pH is monitored and controlled with probes connected via a transmitter to a DCS based process controller. The process is be controlled by addition of $CO_2$ to bring the pH down to set point and addition of alkali to bring pH up to set point. pH is controlled at ±0.03 of set point.

Alkali is added through two addition points to distribute the alkali. This ensures quicker blending of alkali in the event of long recirculation time in the tank. The $CO_2$ is added via the control sparger.

Control and back-up probes are located in the lower port ring at 913 mm (see table 10) from tank bottom. Additionally the pH probes are located diametrically opposite the alkali addition points into the bioreactor.

Bioreactor DOT Control

Dissolved oxygen is monitored and controlled with polarographic DOT probe. The DOT set point maintained by sparging:
Initial $N_2$ ballast and/or air on demand.
Air ballast with air on demand.
Air ballast with oxygen on demand.
Reversing gas usage once oxygen demand decreases.

Cascade DOT control allows DOT set point to be maintained through changes in the ballast and demand gas in conjunction with ramping of agitator speed.

In order to control $pCO_2$ the ballast required to strip out excess $dCO_2$ impacts DOT control. Therefore the DOT control is considered together with $pCO_2$ control for those processes where metabolic $CO_2$ is liberated. DOT is controlled at ±2% of set point. Control and back-up probes are located in the lower port ring at 913 mm from tank bottom.

Bioreactor Dissolved $CO_2$ Control

The process $dCO_2$ is monitored with an $pCO_2$ probe and excess $dCO_2$ is stripped by gassing CA through the ballast sparger. The optimal position for this probe is close to the pH probes.

Feed Addition Control

The feeds (SF22 and amino acid) are high in pH and osmolality. Therefore bolus additions need to be avoided to maintain good pH control. However the control of desired flow rates (±5% of set point) is technically challenging. Therefore an addition strategy that encompasses point of addition with delivery mode avoids the circulation of feed bolus and potential variations of pH control.

Therefore the point of addition is in the plane of the centre-line of the bottom impeller that is 913 mm from tank bottom to assist in the rapid blending of feed bolus.

Antifoam Addition Control

Antifoam (C-emulsion) addition is added as required to maintain the bioreactor liquid surface free of foam. A working stock of 1 in 10 diluted C-emulsion can be dosed on the liquid surface. The antifoam suspension is continuously agitated in the storage container to prevent partitioning. It is important to dose the antifoam close to the centre of the tank to diminish the effects of the radial component of the fluid flow carrying the antifoam to the tank walls where it will adhere. Therefore the addition point is 0.25×T toward the tank centre or 699 mm from tank centre.

Example 2

4000 Liter Bioreactor

Vessel Geometry

The vessel geometry for the 4000 liter bioreactor was determined by an iterative design basis in which the maximum working volume, freeboard straight side distance aspect ratio ($H_L/T$) and impeller to tank diameter ratio (D/T) are altered until an acceptable aspect ratio is achieved.

Bioreactor Aspect Ratio $H_L/T$

Table 11 describes the aspect ratios in the 4000 liter bioreactor at the various operating volumes during normal processing. These aspect ratios arise from the selection of tank ID and the operating volume required. From a processing perspective the mixing requirements at the three operating conditions are different. During preinoculation stage the bioreactor mixing is important to allow medium to equilibrate with minimal $K_La$ requirement. However for post-inoculation and pre-transfer stages both mixing and $K_La$ are important considerations. Therefore both these features were tested at the aspect ratio range.

TABLE 11

Key operating volumes and aspect ratios in the 4000 litre bioreactor

|  | Volume, L | Liquid head, mm | Aspect ratio, $H_L/T$ |
|---|---|---|---|
| Pre-Inoculation | 1.) 1914 | 1.) 1031 | 1.) 0.63 |
|  | 2.) 2782 | 2.) 1448 | 2.) 0.89 |
|  | 3.) 3077 | 3.) 1590 | 3.) 0.98 |
| Post Inoculation & | 1.) 2153 | 1.) 1146 | 1.) 0.70 |
| Pre-transfer | 2.) 3478 | 2.) 1783 | 2.) 1.10 |
|  | 3.) 3846 | 3.) 1960 | 3.) 1.21 |

Tank Diameter

The tank diameter was altered to obtain the optimal aspect ratio $H_L/T$. Changes to tank internal diameter are limited by acceptable aspect ratio and plant footprint. The tank ID is 1626 mm.

Tank Height

Tank height is determined from the maximum operating volume, aspect ratio $H_L/T$, freeboard straight side length, base and top plate design. The final tank height is a compromise value determined from volumetric contingency for foam, plant height and acceptable impeller shaft length. The head to base tan line height is 2817 mm.

Freeboard Height

The freeboard height of 500 mm (1039 liter or 27% v/v of the maximum operating volume) is used for this seed bioreactor.

Head and Base Plate

The base and head plate design is a ASME F&D design for this seed bioreactor.

Bioreactor Agitation Requirement

The agitation of the bioreactor is to achieve rapid mixing, maintain homogeneity, maintain mammalian cells in suspension and gas bubble dispersion. The underlying issue for achieving the above objectives is minimising cell damage through shear forces originating from impeller geometry and eddies or vortices created behind the impeller blades. A compromise of the above objectives was achieved by selection of an appropriate impeller type.

Bottom Versus Top Driven Impeller Shaft

The motor drive is top mounted for the benefits already highlighted.

Baffles

The baffle requirement for centre mounted impeller is critical to prevent vortex formation. The critical issues related to baffles are baffle number, baffle width (W), baffle length ($H_{baffle}$) and baffle to tank wall clearance ($W_c$).

Four equally spaced baffles that are 0.1×T or 163 mm wide 1.1×H–$H_h$ or 2195 mm tall and have a baffle to tank wall clearance, $W_c$ of 0.01×T or 16 mm were used.

The thickness of the baffles is not specified but the thickness needs to ensure rigidity to the radial component of the fluid flow. Additionally thickness needs to ensure the baffle plates are not warped during SIP thereby affecting the baffle to tank wall clearance.

Impeller Type, Size and Number

The impellers for this bioreactor are identically formed to the 20000 liter vessel and have a identical D/T ratio of 0.44. The bottom impeller is a Lightnin's A315 at 710 mm of diameter and the top impeller is a Lightnin's A310 at 710 mm of diameter.

The impeller spacing, $D_c$, $D_s$ and $D_o$

The impeller spacing, $D_s$, between the centre-line of the top impeller and the centre-line of the lower impeller is 1.229×$D_{bottom}$ or 872 mm. The off bottom impeller clearance, $D_c$ is 0.75×$D_{bottom}$ or 531 mm. This allows the lower impeller to remain submerged at the lowest post-inoculation volume of 2153 liters and both impellers submerged at 3367 liters with liquid head above the upper impeller ($D_o$) of 0.5×$D_{top}$ or 358 mm.

Table 12 highlights the volumes that will form liquid surfaces or lower liquid cover above the impeller. Agitation can be modified to avoid foaming at these critical volumes.

TABLE 12

Key operating volumes that cause interaction with impellers and liquid surface

| Interaction | Volume, L | Potential Operation |
|---|---|---|
| Submerge top impeller with 0.5$D_{A310}$ liquid cover | 3433 | Volume seen during inoculation of 1 in 5 processes |
| Liquid surface touching top edge of top impeller | 2758 | Volumes seen during pre-inoculation fill of 1 in 5 processes. |
| Liquid surface touching bottom edge of top impeller | 2621 | Volumes seen during pre-inoculation fill of 1 in 5 processes. |
| Submerge bottom impeller with 0.5$D_{A315}$ liquid cover | 1654 | Volumes seen during pre-inoculation fill of 1 in 5 processes. |
| Liquid surface touching top edge of bottom impeller | 1104 | Volumes seen during pre-inoculation fill of 1 in 5 and 1 in 9 processes. |
| Liquid surface touching bottom edge of bottom impeller | 650 | Volumes seen during pre-inoculation fill of 1 in 5 and 1 in 9 processes. |

[1]Minimum operating volume with lower impeller submerged is 1654 litres and minimum operating volume with both impellers submerged is 3433 litres
[2]The operating volume range is 1914 to 3846 litres.

The 4000 l bioreactor can operate at two discrete post-inoculation volumes with either the lower impeller submerged (during cultivation of 1 in 9 seeding process) or with both impellers submerged (during 1 in 5 seeding process), table 13 shows the liquid cover obtained for the upper and lower impeller during its operation.

A liquid cover of 0.67 to 0.82×$D_{bottom}$ above the lower A315 impeller is observed during cultivation of the 1 in 9 seeded processes. This is within the recommendations of 0.5 to 1×D.

A liquid cover of 0.06 to 0.78×$D_{top}$ above the top A310 impeller is observed during cultivation of 1 in 5 seeded process. The lower liquid cover is outside the recommendation. However this liquid cover is observed during pre-inoculation when mixing and agitation are less critical.

TABLE 13

Key operating volumes and the liquid cover above top impeller, Do and bottom impeller, $D_{Bo}$

| Operating volume, L | Cylinderical height, H (mm) | Do, mm | $D_{Bo}$, mm | Do as ratio of $D_{A310}$ | $D_{Bo}$ as ratio of $D_{A315}$ |
|---|---|---|---|---|---|
| Post-Inoculation and Pre-Transfer, 2153 L | 863 or 34" | — | 614 or 24" | — | $0.82D_{A315}$ |
| Post-Inoculation and Pre-Transfer, 3478 L | 1501 or 59" | 380 or 15" | — | $0.53D_{A310}$ | — |
| Post-Inoculation and Pre-Transfer, 3846 L | 1678 or 66" | 557 or 22" | — | $0.78D_{A310}$ | — |
| Pre-Inoculation, 1914 L | 748 or 29" | — | 499 or 20" | — | $0.67D_{A315}$ |
| Pre-Inoculation, 2782 L | 1166 or 46" | 45 or 2" | — | $0.06D_{A310}$ | — |
| Pre-Inoculation, 3077 L | 1308 or 52" | 187 or 7" | — | $0.26D_{A310}$ | — |

[1]Off bottom impeller clearance, Dc = 531 mm ($0.75D_{A315}$), Impeller separation, Ds = 872 mm ($1.229D_{A315}$), tank ID of 1626 mm and Height of ASME F&D base plate, $H_h$ = 282 mm
[2]Do = H − Ds − (Dc − $H_h$) and $D_{Bo}$ = H − (Dc − $H_h$)

Agitation Rate—Rpm, P/V and Tip Speed

Table 14 specifies the agitation rate for the 4000 liter bioreactor. The bioreactor will be agitated typically at 20-260 W/m$^{-3}$, preferably at 55-85 W/m$^{-3}$. The agitation strategy was developed during the 500 liter pilot fermentations. An agitation rate of 0 to 88±1 rpm is therefore used as an operational range.

TABLE 14

Agitation rate for the 4000 L bioreactor

| Agitation rate, rpm | Power per unit volume, W/m3 | Tip Speed, m/s |
|---|---|---|
| [1]0-88 | 0-150 | 0.0-3.3 |
| [2]0-86 | 0-150 | 0.0-3.2 |

[1]When both impellers submerged
[2]When bottom impeller submerged

Mechanical Seals Specification

A double mechanical seal that is condensate lubricated is used as described.

Bioreactor Aeration Requirement

Table 15 shows the gas flow, based upon scale up of constant superficial gas velocity, for DOT and pH control during the inoculum expansion in the 4000 liter bioreactor. Oxygen is not required for DOT control. However oxygen enriched air can be used to facilitate lower gassing to prevent excess foaming. It is recommended that a smaller range $N_2$ MFC should supply nitrogen for early DOT control and reducing deviant, high levels of DOT.

TABLE 15

Gas flow rate and MFC operating ranges for the 4000 litre bioreactor

| Gas | Operating range | Comments |
|---|---|---|
| Head Space[1] | | |
| 1. Clean air | 1. 0-200SLPM | 1. Head space purging of $CO_2$ and $O_2$ |
| 2. Nitrogen | 2. Utility rated | 2. For rapid DOT probe zeroing |
| 3. Helium | 3. Utility rated | 3. Tank integrity testing |
| Control Sparger | | |
| 1. Clean air[1] | 1. 10-60SLPM | 1. Gas flow under DOT control |
| 2. Oxygen | 2. 1.0-10SLPM | 2. Gas flow under DOT control |
| 3. Carbon dioxide | 3. 1.0-20SLPM | 3. Gas flow under pH control |
| 4. Nitrogen[2] | 4. 2.0-15SLPM | 4. Early DOT control by ballast |
| 5. Helium | 5. Utility rated | 5. Tank integrity testing |

[1]The air and nitrogen gas flow into bioreactor via a bypass for post SIP tank pressurisation.
[2]Nitrogen delivered via the 2 to 15SLPM $N_2$ MFC and could be used during early DOT control The calculation of hole size and number of holes, for the fluted sparger, is iterated until the target Reynolds number of gas emerging from holes is <2000 and the Sauter mean bubble diameter for a bubble chain regime is approximately 10 mm.

Table 16 show the key sparger design specification for the 4000 liter bioreactor. The sparger length, $S_L$ of 568 mm is determined for pipe geometry. The holes are distributed on either end of the sparger to prevent bubble liberating directly under the A315 hub. Alternatively a crescent geometry can be used. The pipe diameter is selected to aid spacing of the desired number of holes. The diameter is 38 mm. The 100 2 mm holes are located on the dorsal surface of the sparger with a single 2 mm hole located on the ventral surface to aid free CIP drainage of the sparger.

The bioreactor port for sparger installation is designed to a fit pipe design of diameter of 38 mm. The position of the port allows the placement of a control sparger at a distance of 194 mm, $D_c$-$S_c$ below the bottom edge of the lower impeller and no greater 337 mm from tank bottom, $S_c$.

TABLE 16

Design specification for the 4000 litre bioreactor sparger

| Parameter | Control Sparger |
|---|---|
| Gas flow, SLPM | 105 |
| Number of sparge holes | 100 |
| Orifice diameter, $d_o$, m | 0.002 |
| Gas flow, $m^3 \cdot s^{-1}$ | 1.75E−03 |
| Orifice area, $m^2$ | 3.14E−06 |
| Total orifice area, $m^2$ | 3.14E−04 |
| Density of air, $Kg \cdot m^{-3}$ | 1.166 |
| Viscosity, $Nm \cdot s^{-2}$ | 1.85E−05 |

TABLE 16-continued

Design specification for the 4000 litre bioreactor sparger

| Parameter | Control Sparger |
|---|---|
| Sauter mean diameter, mm ($d_{vs} = 1.17\, V_o^{0.4}\, d_o^{0.8}\, g^{-0.2}$) | 10.21 |
| Gravitational acceleration, g, m · s$^{-2}$ | 9.807 |
| Density difference, Kg · m$^{-3}$ | 1048.834 |
| Reynold's number, >2000 jetting regime | 704 |
| Gas velocity at sparger, $V_o$, m/s | 5.57 |
| Sparger length, $S_L$, m | 0.568 |
| Combined length to drill required holes, m | 0.2 |
| Number of rows to fit required holes in length $S_L$ | 1 |
| Sparger to tank bottom clearance, Sc, m | 0.337 (13") |
| Sparger to bottom impeller clearance, Dc-Sc, m | 0.194 (8") |

Position of Probes, Addition and Sample Ports

The design basis for positioning of probes, addition and sample ports has been covered in example 1 and are listed in table 17:

TABLE 17

Probe, addition and sampling port specification for the 4000 litre bioreactor

| Probe/Port | Location | [2]Diameter, mm (inches) | [1]Position, mm (inches) | Rational |
|---|---|---|---|---|
| Temperature (main) | Lower ring | 38.1 (1.5") | 1.) 531 (21")<br>2.) 30° | In the plane of centre-line of bottom impeller |
| Temperature (backup) | Lower ring | 38.1 (1.5") | 1.) 531 (21")<br>2.) 170° | In the plane of centre-line of bottom impeller |
| pH (main) | Lower ring | 38.1 (1.5") | 1.) 531 (21")<br>2.) 10° | In the plane of centre-line of bottom impeller |
| pH (backup) | Lower ring | 38.1 (1.5") | 1.) 531 (21")<br>2.) 20° | In the plane of centre-line of bottom impeller |
| DOT (main) | Lower ring | 25.0 (0.98") | 1.) 531 (21")<br>2.) 150° | In the plane of centre-line of bottom impeller |
| DOT (backup) | Lower ring | 25.0 (0.98") | 1.) 531 (21")<br>2.) 160° | In the plane of centre-line of bottom impeller |
| Spare-1 (nutrient) | Lower ring | 25.0 (0.98") | 1.) 531 (21")<br>2.) 170° | In the plane of centre-line of bottom impeller |
| Spare-2 (pCO$_2$) | Lower ring | 38.1 (1.5") | 1.) 531 (21")<br>2.) 180° | In the plane of centre-line of bottom impeller |
| Spare-3 (biomass) | Lower ring | 50.8 (2") | 1.) 531 (21")<br>2.) 190° | In the plane of centre-line of bottom impeller |
| Sample valve (main) | Lower ring | 12.7 (0.5") | 1.) 531 (21")<br>2.) 40° | NovAseptic type |
| Alkali addition | Lower ring | 50.8 (2") | 1.) 531 (21")<br>2.) 190° | Diametrically opposite pH probes |
| Feed 1 | Lower ring | 50.8 (2") | 1.) 531 (21")<br>2.) 200° | Diametrically opposite pH probes |
| Feed 2 | Lower ring | 50.8 (2") | 1.) 531 (21")<br>2.) 210° | Diametrically opposite pH probes |
| Antifoam addition | Head plate | 50.8 (2") | 1.) N/A<br>2.) 170° | Liquid surface/ 0.25T from tank centre |
| Spare surface addition | Head plate | 50.8 (2") | 3.) N/A<br>4.) 180° | Liquid surface directed to vessel wall |
| DOT control sparger orifice | N/A | 50.8 (2") | 337 (13")<br>1.) 0° | |
| Overlay gas | Head plate | 101.6 (4") | 1.) N/A<br>2.) 135° | Diametrically opposite vent out |
| Exhaust vent out | Head plate | 50.8 (2") | 1.) N/A<br>2.) 315° | Diametrically opposite overlay gas in |
| Transfer valve | Base plate | 76.2 (3.0") | 1.) N/A<br>2.) Centre | NovAseptic type to allow free draining |
| Inoculum transfer from 1000 L to 4000 L | Head plate | 101.6 (4") | 1.) N/A<br>2.) 320° | Directed into vessel wall |
| Media inlet | Head plate | 101.6 (4") | 3.) N/A<br>4.) 310° | Directed into vessel wall |

TABLE 17-continued

Probe, addition and sampling port specification for the 4000 litre bioreactor

| Probe/Port | Location | ²Diameter, mm (inches) | ¹Position, mm (inches) | Rational |
|---|---|---|---|---|
| CIP - Spray ball | Impeller flange plate | 76.2 (3") | 1.) N/A  2.) 270° | CIP'ing of highest point |
| CIP - Spray ball | Head plate | 76.2 (3") | 1.) N/A  2.) 60° | |
| CIP - Spray ball | Head plate | 76.2 (3") | 1.) N/A  2.) 180° | |
| CIP - Spray ball | Head plate | 76.2 (3") | 1.) N/A  2.) 300° | |
| Pressure indicating transmitter (PIT) | Head plate | 38.1 (1.5") | 1.) N/A  2.) 60° | |
| Pressure gauge | Head plate | 38.1 (1.5") | 1.) N/A  2.) 50° | |
| Rupture disc | Head plate | 101.6 (4") | 1.) N/A  2.) 280° | |
| Spare nozzle | Head plate | 101.6 (4") | 1.) N/A  2.) 160° | |
| Sight glass | Head plate | 101.6 (4") | 1.) N/A  2.) 70° | |
| Light glass | Head plate | 76.2 (3") | 1.) N/A  2.) 75° | |
| Agitator head/flange | Head plate | 813 (32") | N/A | Entry/removal |
| Impeller shaft and seal manway | Agitator head/ flange | 152 (6") | N/A | Entry/removal |

[1]Measured from the tangential line of the base plate. Degrees pertain to plane of clockwise rotation.
[2]Diameter of nozzle at bioreactor.

Addition Ports, Surface and Sub-Surface

The need to categorise additions ports that terminate at liquid surface and those that are subsurface is determined by the operational scenarios and effects of feed strategy on process control.

The 4000 liter bioreactor has been designed to accept two subsurface feeds and alkali that need to be discharged in well-mixed area of the bioreactor. The foam is controlled by surface addition of 1 in 10 diluted C-emulsion. A single spare above surface addition port directed to the vessel wall is also designed for future flexibility. The splashing of culture onto the surface of the medium during inoculation of the seed bioreactor can be avoided to prevent build up of foam. Therefore the inoculum addition port is above surface and directed to the vessel wall. The use of the harvest port in the base plate is the ideal port for removal of inoculum during transfer of inoculum. Additionally the medium addition port is directed to the vessel wall. In summary the total addition ports are:

Four surface additions with medium inlet, inoculum inlet and a spare small addition directed to the vessel wall and addition port for antifoam dropped on to the liquid surface away from the vessel wall.

Three subsurface additions for feeds and alkali.

Sample Ports

The sample port design is similar to that specified for the 20 000 liter bioreactor.

Volume Measurement

The level sensor is able to measure up to 4000 liters with an accuracy ±0.5% of full span.

Bioreactor Temperature Control

The 1914 to 3077 liter of medium are brought to operating temperature, typically 36.5° C. by process control. This is achieved by "gentle" heating of the jacket and avoid high temperature at vessel wall.

Jacket

The bioreactor jacket area is specified with the following considerations in mind:

Steam sterilisation at 121-125° C.

Warming up of 1914-3077 liters of medium from 10° C. to 36.5° C. in <2 h.

All points within the bioreactor must reach ±0.2° C. of set point, typically 36.5° C. as measured by thermocouples.

Chilling of 1914-3077 liters of medium from 36±2° C. to 10° C. in 2 h.

Bioreactor pH Control

The process pH is monitored and controlled with probes connected via a transmitter to a DCS based process controller. The process pH is controlled by addition of $CO_2$ through the control sparger to bring the pH down to set point and addition of alkali to bring pH up to set point.

Alkali is added through at least one subsurface port at centre-line of the bottom impeller. The $CO_2$ will be added via the control sparger.

Control and backup probes are in the lower port ring at 531 mm from tank bottom as shown in table 17.

Bioreactor DOT Control

Dissolved oxygen is monitored and controlled with polarographic DOT probe. The DOT set point maintained by sparging:

Initial $N_2$ ballast and/or air on demand.

Air ballast with air on demand.

Air ballast with oxygen on demand.

DOT control allows DOT set point to be maintained through interchangeable use of oxygen or air as demand gas. It is not envisaged that $pCO_2$ control is required in the inoculum bioreactor. Control and backup probes are in the lower port ring at 531 mm from tank bottom as shown in table 17.

Feed Addition Control

The point of addition is 531 mm from tank bottom, in the plane of the centre-line of the lower impeller to assist in the rapid dissipation of feed bolus.

Antifoam Addition Control

The addition point is at surface projecting 0.25×T toward the tank centre or 407 mm from centre of tank.

Example 3

1000 Liter Bioreactor Specification

Vessel Geometry

The vessel geometry for the 1000 liter bioreactor was determined by an iterative design basis in which the maximum working volume, freeboard straight side distance, aspect ratio ($H_L/T$) and impeller to tank diameter ratio (D/T) are altered until an acceptable aspect ratio is achieved.

Bioreactor Aspect Ratio $H_L/T$

Table 18 below describes the aspect ratios in the 1000 liter bioreactor at various operating volumes during normal processing. These aspect ratios arise from the selection of tank ID and the operating volume required. From a processing perspective the mixing requirements at the different operating conditions are different. During preinoculation stage the bioreactor mixing is important to allow medium to equilibrate with minimal $K_La$ requirement. However with post-inoculation and pre-transfer stages both mixing and $K_La$ are important considerations. Therefore both of these features were tested at the aspect ratio range.

TABLE 18

Key operating volumes and aspect ratios in the 1000 litre bioreactor

| | Volume, L | Liquid head, mm | Aspect ratio, $H_L/T$ |
|---|---|---|---|
| Stage N-3 | | | |
| Pre-Inoculation Stage N-3 | 250 | 484 | 0.56 |
| Post Inoculation & Pre-transfer/Harvest Stage N-2 | 300 | 570 | 0.66 |
| Pre-Inoculation, Post-drain Pre-refill Stage N-2 | 1.) 400[1]<br>2.) 50-100[1]<br>3.) 192[2] | 1.) 740<br>2.) 143-228<br>3.) 385 | 1.) 0.86<br>2.) 0.17-0.26<br>3.) 0.45 |
| Post Inoculation & Pre-transfer/Harvest | 1.) 450<br>2.) 450-900[3]<br>3.) 960[4] | 1.) 826<br>2.) 826-1594<br>3.) 1696 | 1.) 0.96<br>2.) 0.96-1.84<br>3.) 1.96 |

[1]Pre-inoculation volume and rolling seed inoculation volume for the 1 in 9 sub-cultivation process.
[2]Rolling seed inoculation volume for the 1 in 5 sub-cultivation processes.
[3]Rolling seed post inoculation & pre-transfer volume for the 1 in 9 sub-cultivation processes.
[4]Rolling seed post inoculation & pre-transfer volume for the 1 in 5 sub-cultivation processes.

Tank Diameter

The tank diameter is altered to obtain the optimal aspect ratio $H_L/T$. Changes to tank internal diameter are limited by acceptable aspect ratio and plant footprint. The tank ID is 0.864 m.

Tank Height

The tank height is determined from the maximum operating volume, aspect ratio $H_L/T$, freeboard straight side length, base and top plate design. The final tank height is a compromise value determined from volumetric contingency for foam, plant height and acceptable impeller shaft length. The head to base tangent line height is 2.347 m.

Freeboard Height

The freeboard height of 500 mm (293 liters or 31% v/v of the maximum operating volume) is used for this seed bioreactor.

Head and Base Plate

The base and head plate design is ASME F&D for this seed bioreactor.

Bioreactor Agitation Requirement

Agitation of the bioreactor is to achieve rapid mixing, maintain homogeneity, maintain mammalian cells in suspension and gas bubble dispersion. The underlying issue with achieving the above objectives is to minimise cell damage through shear forces originating from impeller geometry and "eddies" or vortices created behind the impeller blades. A compromise of the above objectives was achieved by selection of an appropriate impeller type and gassing strategy.

Bottom Versus Top Driven Shaft

The motor drive is top mounted for the benefits as already highlighted.

Baffles

The baffle requirement for a centre mounted impeller is critical to prevent vortex formation. The critical issues related to baffles are baffle number, baffle width (W), baffle length ($H_{baffle}$) and baffle to tank wall clearance ($W_c$).

Four equally spaced baffles that are 0.1×T or 86 mm wide 1.1×H–$H_h$ or 2099 mm tall and have a baffle to tank wall clearance, $W_c$ of 0.01×T or 9 mm were used.

The thickness of baffle is not specified but the thickness needs to ensure rigidity to the radial component of the fluid flow. Additionally thickness needs to ensure the baffle plates are not warped during SIP thereby affecting the baffle to tank wall clearance.

Impeller Type, Size and Number

The impellers for the 1000 l bioreactor should be identical formed to the 20 000 liter vessel with an identical D/T ratio. Therefore the bottom impeller is a Lightnin's A315 at 381 mm diameter and the top impeller is a Lightnin's A310 at 381 mm diameter.

The Impeller Spacing, $D_c$, $D_s$ and $D_o$

The impeller spacing ($D_s$) between the centre-line of the top impeller and the centre-line of the bottom impeller is 2×$D_{bottom}$ (762 mm). The off bottom impeller clearance ($D_c$) is 0.4×$D_{bottom}$ (152 mm). This allows the bottom impeller to remain submerged with liquid cover ($D_o$) of 0.5×$D_{bottom}$ or 190 mm at the lowest post-inoculation volume of 167 liters and both impeller submerged at 616 liters with liquid head above the upper impeller, $D_o$, of 0.5×$D_{top}$ (190 mm).

Table 19 highlights volumes that will form liquid surfaces or lower liquid cover above the impeller Agitation can be modified to avoid foaming at these critical volumes.

TABLE 19

Key operating volumes that cause interaction with impellers and liquid surface

| Interaction | Volume, L | Potential Operation |
|---|---|---|
| Submerge top impeller with $0.5D_{A310}$ liquid cover | 616 | Volume seen during inoculation of 1 in 5 processes and rolling operation of the 1 in 9 process |
| Liquid surface touching top edge of top impeller | 512 | Volume seen during inoculation of 1 in 5 processes and rolling operation of the 1 in 9 process |
| Liquid surface touching bottom edge of top impeller | 492 | Volume seen during inoculation of 1 in 5 processes and rolling operation of the 1 in 9 process |
| Submerge bottom impeller with $0.5D_{A315}$ liquid cover | 167 | Volume seen during inoculation of 1 in 5 processes and rolling operation of the 1 in 9 process |
| Liquid surface touching top edge of lower impeller | 90 | Volume seen during rolling operation of the 1 in 9 process |
| Liquid surface touching bottom edge of lower impeller | 21 | Volumes seen during pre-inoculation fill of 1 in 5 and 1 in 9 processes. |

The 1000 l bioreactor operates at two discrete post-inoculation volumes with either the bottom impeller submerged during the 1 in 5 processes and 1 in 9 processes or with both impellers submerged during the N-2 phase of the 1 in 5 process and rolling seed operations for both 1 in 5 and 1 in 9 processes.

Table 20 shows the liquid cover above the upper and lower impeller during operation of the 1 in 5 and 1 in 9 sub-cultivation processes. During rolling operation of the 1 in 5 and 1 in 9 processes the liquid cover above the lower impeller falls below 0.5×D. It is therefore important to reduce the agitation rate, to avoid surface gas entrainment, whilst operating at this low volume. At 960 liters a liquid cover, ($D_o$) of 2.05×Dtop is obtained. At this level $K_La$ has been shown not to be adversely affected and bulk blending is not an issue.

TABLE 20

Key operating volumes and the liquid cover above top impeller, Do and bottom impeller, $D_{Bo}$

| Operating volume, L | Cylinderical height, H (mm) | Do, mm | $D_{Bo}$, mm | Do as ratio of $D_{A310}$ | $D_{Bo}$ as ratio of $D_{A315}$ |
|---|---|---|---|---|---|
| Pre-Inoculation, 250 L | 334 | — | 332 | — | $0.87D_{A315}$ |
| Pre-Inoculation, 400 L | 590 | — | 588 | — | $1.54D_{A315}$ |
| Post-Inoculation and Pre-Transfer, 300 L | 419 | — | 417 | — | $1.10D_{A315}$ |
| Post-Inoculation and Pre-Transfer, 450 L | 675 | — | 673 | — | $1.77D_{A315}$ |
| Post drain, pre-bulk 192 L | 235 | — | 233 | — | $0.61D_{A315}$ |
| Post drain, pre-bulk 50-100 L | 0-78 | — | 76 | — | $0.2D_{A315}$ |
| Post-Inoculation and Pre-Transfer, 900 L | 1443 | 679 | — | $1.78D_{A310}$ | — |
| Post-Inoculation and Pre-Transfer, 960 L | 1545 | 782 | — | $2.05D_{A310}$ | — |

(1) Off bottom impeller clearance, Dc = 152 mm ($0.4D_{A315}$), Impeller separation, Ds = 762 mm ($2D_{A315}$), tank ID of 864 mm and Height of ASME F&D base plate, $H_h$ = 151 mm
(2) Do = H − Ds − (Dc − $H_h$) and $D_{Bo}$ = H − (Dc − $H_h$)

Agitation Rate—Rpm, P/V and Tip Speed

Table 21 specifies the agitation rate for the 1000 liter bioreactor. The bioreactor is agitated at around 20-260 W/m³, preferably at 55-85 W/m³. The agitation strategy was developed during the 500 liter pilot fermentations. An agitation rate of up to 155±1 rpm is used as an operational range.

TABLE 21

Agitation rate for the 1000 L bioreactor

| Agitation rate, rpm | Power per unit volume, W · m⁻³ | Tip Speed, m · s⁻¹ |
|---|---|---|
| ¹0-155 | 0-150 | 3.1 |
| ²0-145 | 0-145 | 2.9 |

¹When both impellers submerged
²When bottom impeller submerged

Mechanical Seals Specification

A double mechanical seal that is condensate lubricated as described was used.

Bioreactor Aeration Requirement

Table 22 shows the gas flows based upon scale up of constant superficial gas velocity, for DOT and pH control during the inoculum expansion in the 1000 liter bioreactor. Oxygen will not be required for DOT control. However oxygen enriched air may be used to facilitate lower gassing to prevent excess foaming. It is recommended that the smaller range CA MFC should be used to delivery nitrogen for early DOT control and reducing deviant, high levels of DOT.

TABLE 22

Gas flow rate and MFC operating ranges for the 1000 litre bioreactor

| Gas | Operating range | Comments |
|---|---|---|
| Head Space[1] | | |
| 1. Clean air | 1. 0-50 SLPM | 1. Head space purging of $CO_2$ and $O_2$ |
| 2. Nitrogen | 2. Utility rated | 2. For rapid DOT probe zeroing |
| 3. Helium | 3. Utility rated | 3. Tank integrity testing |
| Control Sparger | | |
| 1. Clean air[1] | 1. 2-20SLPM | 1. Gas flow under DOT control |
| 2. Oxygen | 2. 0.2-5SLPM | 2. Gas flow under DOT control |
| 3. Carbon dioxide | 3. 0.2-10SLPM | 3. Gas flow under pH control |
| 4. Nitrogen[2] | 4. 0.2-5SLPM | 4. Early DOT control by ballast |
| 5. Helium | 5. Utility rated | 5. Tank integrity testing |

[1]The air and nitrogen gas flow into bioreactor via a bypass for post SIP tank pressurisation.
[2]Nitrogen delivered via the 0 to 5SLPM CA MFC, could be used during early DOT control.

The calculation of hole size and number is iterated until the target Reynolds number of gas emerging from holes is <2000 and the Sauter mean bubble diameter for a bubble chain regime is approximately 10 mm.

Table 23 shows the key sparger design specification for the 1000 liter bioreactor. The sparger length, $S_L$ of 305 mm is determined for pipe geometry. The holes are distributed on either end of the sparger to prevent bubble liberating directly under the A315 hub. Alternatively a crescent geometry can be considered.

The pipe diameter is 25 mm. 30 2 mm holes are located on the dorsal surface of the sparger with a single 2 mm hole located on the ventral surface to aid free CIP drainage of the sparger.

The bioreactor port for sparger installation is designed to fit pipe design of diameter of 25 mm. The position of port allows the placement of control sparger at a distance of 88 mm ($D_c$-$S_c$) below the bottom edge of the bottom impeller and no greater than 64 mm from tank bottom ($S_c$).

TABLE 23

Design specification for 1000 litre bioreactor spargers

| Parameter | Control Sparger |
|---|---|
| Gas flow, SLPM | 35 |
| Number of sparge holes | 30 |
| Orifice diameter, $d_o$, m | 0.002 |
| Gas flow, $m^3 \cdot s^{-1}$ | 5.83E-04 |
| Orifice area, $m^2$ | 3.14E-06 |
| Total orifice area, $m^2$ | 9.42E-05 |
| Density of air, $Kg \cdot m^{-3}$ | 1.166 |
| Viscosity, $Nm \cdot s^{-2}$ | 1.85E-05 |
| Sauter mean diameter, mm | 10.65 |
| ($d_{vs} = 1.17 \, V_o^{0.4} \, d_o^{0.8} \, g^{-0.2}$) | |
| Gravitional acceleration, g, $g \, m \cdot s^{-2}$ | 9.807 |
| Density difference, $Kg \cdot m^{-3}$ | 1048.834 |
| Reynold's number, >2000 jetting regime | 782 |
| Gas velocity at sparger, $V_o$, m/s | 6.19 |
| Sparger length, $S_L$, m | 0.305 |
| Combined length to drill required holes, m | 0.06 |
| Number of rows to fit required holes in length $S_L$, m | 1 |
| Sparger to tank bottom clearance, Sc, m | 0.064 |
| Sparger to bottom impeller clearance, Dc-Sc, m | 0.088 |

Position of Probes, Addition and Sample Ports

The design basis for positioning of probes, addition and sample ports is the same as for the 20 000 l bioreactor.

TABLE 24

Probe, addition and sampling port specification for the 1000 litre bioreactor

| Probe/Port | Location | Diameter, mm (inches) | [1]Position, mm (inches) | Rational |
|---|---|---|---|---|
| Temperature (main) | Lower ring | 38.1 (1.5") | 1. 286 (11") 2. 30° | Positioned to minimise monitored volume |
| Temperature (backup) | Lower ring | 38.1 (1.5") | 1. 286 (11") 2. 170° | Positioned to minimise monitored volume |
| PH (main) | Lower ring | 38.1 (1.5") | 1. 286 (11") 2. 10° | Positioned to minimise monitored volume |
| PH (backup) | Lower ring | 38.1 (1.5") | 1. 286 (11") 2. 20° | Positioned to minimise monitored volume |
| DOT (main) | Lower ring | 25.0 (0.98") | 1. 286 (11") 2. 150° | Positioned to minimise monitored volume |
| DOT (backup) | Lower ring | 25.0 (0.98") | 1. 286 (11") 2. 160° | Positioned to minimise monitored volume |
| Spare-2 (spare - $pCO_2$) | Lower ring | 38.1 (1.5") | 1. 286 (11") 2. 180° | Positioned to minimise monitored volume |
| Spare-3 (spare - Biomass) | Lower ring | 50.8 (2") | 1. 286 (11") 2. 190° | Positioned to minimise monitored volume |
| Sample valve (main) | Lower ring | 38.1 (1.5") | 1. 286 (11") 2. 40° | NovAseptic type |
| Sample valve (back up) | Lower ring | 38.1 (1.5") | 1. 286 (11") 2. 40° | NovAseptic type |
| Alkali addition | Lower ring | 12.7 (0.5") | 1. 286 (11") 2. 190° | Diametrically opposite pH probes |
| Feed 1 | Lower ring | 12.7 (0.5") | 1. 286 (11") 2. 200° | Diametrically opposite pH probes |
| Feed 2 | Lower ring | 12.7 (0.5") | 1. 286 (11") 2. 210° | Diametrically opposite pH probes |
| Antifoam addition | Head plate | 50.8 (2") | 1. N/A 2. 170° | Liquid surface/0.25T from tank centre |
| Spare surface addition | Head plate | 50.8 (2") | 1. N/A 2. 180° | Liquid surface directed to vessel wall |
| DOT control sparger orifice | N/A | 50.8 (2") | 1. 64 (2.5") 2. 0° | |

TABLE 24-continued

Probe, addition and sampling port specification for the 1000 litre bioreactor

| Probe/Port | Location | Diameter, mm (inches) | [1]Position, mm (inches) | Rational |
|---|---|---|---|---|
| Overlay gas | Head plate | 38.1 (1.5") | 1. N/A<br>2. 135° | Diametrically opposite vent out |
| Exhaust vent out | Head plate | 38.1 (1.5") | 1. N/A<br>2. 315° | Diametrically opposite overlay gas in |
| Transfer valve | Base plate | 50.8 (2.0") | 1. N/A<br>2. Centre | NovAseptic type to allow free draining |
| Media inlet | Head plate | 76.2 (3") | 1. N/A<br>2. 310° | Directed into vessel wall |
| Inoculum transfer from S200 to 1000 L | Head plate | 50.8 (2.0") | 1. N/A<br>2. 320° | Directed into vessel wall |
| CIP - Spray ball | Head plate | 76.2 (3") | 1. N/A<br>2. 270° | CIP'ing of highest point |
| CIP - Spray ball | Head plate | 76.2 (3") | 1. N/A<br>2. 60° | |
| Pressure gauge | Head plate | 38.1 (1.5") | 1.) N/A<br>2.) 50° | |
| Rupture disc | Head plate | 50.8 (2") | 1.) N/A<br>2.) 280° | |
| Spare nozzle | Head plate | 101.6 (4") | 1.) N/A<br>2.) 160° | |
| 1. Hand hole<br>2. Sight glass | Head plate | 1. 203.2 (8")<br>2. 101.6 (4") | 1.) N/A<br>2.) 70° | Single port permitting two functions |
| Agitator shaft opening | Head plate | 152.4 (6") | 1.) N/A<br>2.) 75° | Centre of head plate |

[1]Measured from the tangential line of the base plate. Degree pertains to plane of clockwise rotation.
[(2)] Diameter of nozzle at the bioreactor In order to monitor, control and sample from a volume of 50 l, the probes and port ring needs to be 151 mm from tank bottom. However the probe/port ring cannot be located this low as it falls on the weld of the base plate and the straight cylindrical side of the bioreactor. The probe and port ring has been specified at 286 mm from tank bottom. This permits a volume of 134 liters to be monitored, controlled and sampled. The probes/port ring is located as close to the tank bottom as permitted to minimise the monitored/controlled volume.

Addition Ports, Surface and Sub-Surface

The 1000 liter bioreactor has been designed to accept two subsurface feeds and alkali to be discharged into a well-mixed area of the bioreactor. The foam is controlled by surface addition of 1 in 10 diluted C-emulsion. A single above surface spare addition port directed to the vessel wall was also integrated for future flexibility. The splashing of culture on to the surface of the medium during inoculation of seed bioreactor should be avoided to prevent build up of foam. Therefore the inoculum addition port is above surface and directed to the vessel wall. The use of the harvest port in the base plate is the ideal port for removal of inoculum during transfer of inoculum. Additionally the medium addition port is directed on to the vessel wall. In summary the total addition ports are:

Four surface additions with medium inlet, inoculum inlet and a spare small addition directed to the vessel wall and addition port for antifoam dropped on to the liquid surface away from the vessel wall.

Three subsurface additions for feeds and alkali.

Sample Ports

The sample port design is similar to that specified for the 20 000 liter bioreactor. The sample port is located 286 mm from tank bottom to minimise the volume that can be sampled.

Volume Measurement

The level sensor is able to measure up to 1000 liters. The level sensor sensitivity is at least 0.25% of full span.

Bioreactor Temperature Control

The 250 to 800 liters of medium is brought to operating temperature, typically 36.5° C. during initial inoculation and "seed rolling operation" by process control. This is achieved by "gentle" heating of the jacket and avoid high temperature at vessel wall.

Jacket

The bioreactor jacket area is specified with the following considerations in mind:

Steam sterilisation at 121-125° C.
Warming up of 250-800 liters of medium from 10° C. to 36.5° C. in <2 hrs.
All points within the bioreactor must reach ±0.2° C. of set point, typically 36.5° C. as measured by thermocouples.
Chilling of 400 liters of medium from 36±2° C. to 10° C. in 2 hrs.

Bioreactor pH Control

The process pH is monitored and controlled with probes connected via a transmitter to a DCS based process controller. The process pH is controlled by addition of $CO_2$ to bring the pH down to set point and addition of alkali to bring pH up to set point. Alkali is added through at least one subsurface port at centre-line of the bottom impeller. The $CO_2$ is added via the control sparger.

The control and back up probes are in the lower port ring at 286 mm from tank bottom to minimise the volume that can be monitored as shown in Table 24.

Bioreactor DOT Control

Dissolved oxygen is monitored and controlled with polarographic DOT probe. The DOT set point maintained by sparging:—

Initial $N_2$ ballast and/or air on demand
Air ballast with air on demand
Air ballast with oxygen on demand DOT control allows DOT set point to be maintained through interchangeable use of oxygen or air as demand gas.

Control and back up probes are in the lower port ring at 286 mm from tank bottom minimise the volume that can be monitored, as shown in table 24.

Feed Addition Control

The point of addition is 286 mm from tank bottom, in the vicinity of the centre-line of the bottom impeller to assist in the rapid dissipation of feed bolus.

Antifoam Addition Control

The addition point is at surface projecting 0.25×T toward the tank centre or 216 mm from tank centre.

Example 4

Bioreactor Train

The bioreactor design is based on the ability to perform both 1 in 5 (20% v/v) and 1 in 9 (11% v/v) subculture ratios. The bioreactor train consists of a 1000 liter (Stages N-3 and N-2) and 4000 liter (Stage N-1) seed bioreactors followed by a 20 000 liter production bioreactor (Stage N). The operating volumes for each bioreactor are defined in examples 1 to 3. The bioreactors are based on a stirred tank design and a top driven agitator system was used.

The design is based on the need to ensure a homogenous environment with respect to process parameters such as pH, dissolved oxygen tension (DOT) and temperature, maintaining a well mixed cell suspension and blending nutrient feeds within the bioreactor. This provides the necessary physico-chemical environment for optimal cell growth, product accumulation and product quality. Key to the design philosophy is the need to maintain geometric similarity. This allows a scale down model to be developed at 12 liter laboratory and 500 liter pilot scales. The design of the seed and production bioreactors are based on the same principles although some departures are required to allow for flexibility in processing. The aspect ratios ($H_L/T$) selected are typical of those used in mammalian cell culture and are in the range 0.17 to 1.96 post-inoculation.

TABLE 25

Key bioreactor design parameters

| | 1000 litre | 4000 litre | 20000 litre |
|---|---|---|---|
| Aspect ratio ($H_L/T$) | 0.17-1.96 | 0.63-1.21 | 0.83-1.34 |
| Impeller to tank diameter (D/T) | 0.44-0.46 | 0.44-0.46 | 0.44-0.46 |
| Operating Volume (L) | 50-960 | 1914-3846 | 13913-21739 |
| Agitator speed (rpm) | 0-155 | 0-88 | 0-80 |
| Control sparger CA (SLPM) | 2-20 | 0-60 | 0-1000 |
| Ballast sparger CA/$N_2$ flow (SLPM) | No ballast sparger | No ballast sparger | 0-500 |
| Cultivation residence time (days) | 2-5[1] | 2-5 | 10-15 |
| Feed additions | 2 surface 3 sub-surface | 2 surface 3 sub-surface | 4 surface 4 sub-surface |

[1] The culture residence time in 1000 litre bioreactor may be higher depending on the length of time the bioreactor is repeatedly sub-cultivated or "rolled".

The design constraint is based upon a seeding ratio of 11% v/v (1 in 9 dilution) and 20% v/v (1 in 5 dilution), with feed application of 4% v/v to 25% v/v of the post-inoculation volume. The post-inoculation volume in the production bioreactor is adjusted for feed applications up to 15% such that after the addition of all the feeds the final volume at harvest ends up at 20 000 l. However for feed applications greater then 15% v/v the post-inoculation volume is adjusted for a 15% v/v feed but following the application of feeds the final pre-harvest volume will be a minimum of 20 000 and a maximum 22 000 liters. The production bioreactor is expected to hold a total of 20 000 to 22 000 liters at the end of a batch. Table 26 shows the preinoculation volume, inoculation volume and transfer or harvest volume for each of the three inoculum expansion stages and the production bioreactor.

The seed bioreactors (stage N-1 to N-3) are unlikely to be fed therefore the maximum operating volume will be at inoculation. The operating volume range for the 4000 liter seed bioreactor (stage N-1) is 1914 to 3846 liters. In order to design a bioreactor that can grow cells from 20% v/v seed split ratio, the 1000 liter seed bioreactor (stages N-2 and N-3) will operate at two operating ranges. For the 11% v/v seed split ratio the bioreactor train can produce sufficient culture to meet forward processing cell concentration criteria in a single expansion/sub-cultivation stage. However the bioreactor train requires two expansion/sub-cultivation stages to meet forward processing criteria for 20% v/v seed split ratio process. Thus for 11% v/v seed split ratio process an operating range of 400 to 450 liters is required and for the 20% v/v seed split ratio process an operating volume range of 250 to 960 liters is required.

TABLE 26

Vessel sizes for bioreactor train

| | 1000 litre | | 4000 litre | 20000 litre |
|---|---|---|---|---|
| Stage | N-3 | N-2 | N-1 | N |
| 11% v/v Seed with 4 to 25% v/v production feed | | | | |
| Pre-inoculation Volume (L) | 400 | — | 1914 | 15456-17096 |
| Inoculation Volume (L) | 450 | — | 2153 | 17391-19231 |
| Transfer or Harvest Volume (L) | 450 | — | 2153 | 20000-21739 |
| 20% v/v Seed with 4 to 25% v/v production feed | | | | |
| Pre-inoculation Volume (L) | 250 | 768 | 2782-3077 | 13913-15385 |
| Inoculation Volume (L) | 300 | 960 | 3478-3846 | 17391-19231 |
| Transfer or Harvest Volume (L) | 300 | 960 | 3478-3846 | 20000-21739 |
| Assumed operating volume | | | | |
| Minimum Volume (L) | 250 | | 1914 | 13913 |
| Maximum Volume (L) | 960 | | 3846 | 21739 |
| Ratio of Maximum volume/Minimum volume | 3.84 | | 2.01 | 1.56 |

It is recommended that the 1000 liter seed bioreactor is inoculated from culture produced in an S200 Wave bioreactor.

1000 l: This bioreactor is operated in batches of up to 5 days, with potential "shot additions" of feeds, for cultivation of mammalian cells. However due to repeated drain and refill operation at the end of each batch the total process residence time in this bioreactor can exceed 30 days. The mammalian cells are kept in a homogeneous suspension by agitation via an identical impeller system to the 20 000 liter bioreactor. Additionally other features will be kept geometrically similar to the 20 000 liter bioreactor, where possible.

Sparging air or oxygen and air or nitrogen respectively will control process DOT. Process pH is controlled by addition of alkali for base control and of sparged $CO_2$ for acid control.

The process operating volume of the bioreactor changes at different phases of operation. Initially the bioreactor is aseptically filled with a bolus of medium at 250 to 400 liters in 0.5 h. The bioreactor is operated in a pre-inoculation phase to bring the process variables to predefined set points. 50 liter culture from a (N-4) S-200 seed wave bioreactor is inoculated, by pneumatic assisted flow, or pumped with a peristaltic pump in 25 to 30 minutes into the 1000 liter bioreactor at 1 in 5 or 1 in 9 dilutions. The post-inoculation operating volume is 300 and 450 liters for 1 in 5 and 1 in 9 seeded process respectively. The addition of alkali for base control and 1 in 10 antifoam suspension for suppression of foam contributes towards the final volume. The inoculum culture may be fed by a "shot addition" if the culture interval is longer then expected. As a result of mixing and gassing the liquid volumes described above will expand due to gas hold up. The extent of this rise is dependent on the sparger type used, power per unit volume imparted by impellers and superficial gas velocity of sparged gasses.

The N-3 stage ends when viable cell concentration reaches transfer criteria. The N-2 stage for 1 in 5 process begins with a bulk up in volume to 960 liter by draining of 192 liter excess culture and addition of 768 liter fresh medium in 1.5 h. 696 to 769 liter of culture are transferred at the end of N-2 stage to the 4000 liter bioreactor for the 1 in 5 processes. For the 1 in 9 processes 239 liters are transferred to the 4000 liter bioreactor.

The 1000 l bioreactor is continuously "drained and refilled with fresh medium" or "rolled" to provide back up culture for the 4000 liter bioreactor. The duration of the rolling seed operation is dependent on the length of the production campaign and the permissible elapsed generations number of the seed culture. Typically it is assumed that rolling seed operation is in excess of 30 days. The rolling operation consists of retaining approximately 192 liters of the 960 liter culture and diluting with 768 liter fresh medium for the 1 in 5 processes. For the 1 in 9 processes the 1000 liter bioreactor is expected to be "rolled" by retaining 50 to 100 liter of the 450 to 900 liter culture and diluting with 400 to 800 liter fresh medium. Process control ranges are relaxed over this operation. The medium added to the bioreactor during rolling operation is warmed to 30° C.

4000 l: This bioreactor is operated in batch of no more then 5 days, with potential "shot additions" of feeds, for cultivation of mammalian cells. The mammalian cells are kept in a homogeneous suspension by agitation via an identical impeller system described in example 1. Additionally this vessel is geometrically similar to the 20 000 liter bioreactor.

Sparging air or oxygen and air or nitrogen respectively controls process DOT. Process pH is controlled by addition of alkali for base control and of sparged $CO_2$ for acid control.

The process operating volume of the bioreactor changes at different phases of operation. Initially the bioreactor is aseptically filled with a bolus of protein free medium at 1914 to 3077 liters in 1.5 h. The bioreactor operates in a pre-inoculation phase to bring the process variables to pre-defined set points. Culture from the 1000 liter (N-2) seed seed bioreactor is inoculated by pneumatic flow at a flowrate to allow transfer in one hour, at 1 in 5 or 1 in 9 dilutions. The post-inoculation operating volume is 2153 to 3846 liters. The addition of alkali for base control and 1 in 10 antifoam suspension for suppression of foam contributes towards the final volume. The inoculum culture may be fed by a "shot addition" if the culture interval is longer then expected. As a result of mixing and gassing the liquid volume expands due to gas hold up. The extent of this rise is dependent on the sparger type used, power per unit volume imparted by impellers and superficial gas velocity of sparged gasses.

20 000 l: This bioreactor is operated in batch or fed batch mode for 10 to 15 days for the cultivation of mammalian cells. The mammalian cells are kept in a homogeneous suspension by agitation via an impeller system.

The process operating volume of the bioreactor changes at different phases of operation. Initially the bioreactor is aseptically filled with cell culture medium at 13913 to 17096 liters in 1-2 h. The bioreactor is operated in a pre-inoculation phase to bring the process variables to predefined set points. Culture from the 4000 liter seed bioreactor (N-1) is inoculated by pneumatic flow at a flow rate range of <4000 l/h into the 20 000 liter bioreactor at 1 in 5 or 1 in 9 dilutions. The post-inoculation volume continuously increases following an application of sub-surface feeds to maximum of 20 000 liters (two feeds totaling 4 to 25% v/v). The addition of alkali for base control and 1 in 10 antifoam suspension for suppression of foam accounts for about 100 liters and 20 liters respectively. As a result of mixing and gassing the liquid volume expands due to gas hold up. The extent of this rise is depended on the sparger type used (fluted or sintered), power per unit volume imparted by impellers and superficial gas velocity of sparged gasses.

Table 27 describes the aspect ratios in the 20 000 liter bioreactor at various operating volumes during normal processing. The aspect ratios have been tested at 500 liter scale and provided the superficial gas velocity and power per unit volume are kept constant the $K_La$ remains constant.

TABLE 27

Key operating volumes and aspect ratios in the 20 000 litre bioreactor

| | Volume, L | Liquid head, mm | Aspect ratio, $H_L/T$ |
|---|---|---|---|
| Pre-Inoculation | 13913-17096 | 2458-2977 | 0.88-1.07 |
| Post Inoculation | 17391-19231 | 3025-3325 | 1.08-1.19 |
| Harvest | 20000-21739 | 3451-3734 | 1.23-1.34 |

What is claimed is:

1. A method for cultivating and propagating mammalian cells, comprising cultivating at least one mammalian cell under suitable conditions and in a suitable culture medium in a bioreactor for the cultivation of mammalian cells, wherein the bioreactor is a self-supporting biocompatible tank having a volume of at least 4000 l and at least one top impeller and at least one bottom impeller, and wherein the at least one top impeller is a hydrofoil impeller, and wherein an impeller spacing ($D_s$) between the top impeller and the bottom impeller is at least 1.229× the diameter of the bottom impeller ($D_{bottom}$) and at most 2×$D_{bottom}$, wherein a liquid height above the top impeller ($D_o$) is at least 0.3× the diameter of the top impeller ($D_{top}$) and at most 2.5×Dtop, and wherein a bottom clearance ($D_c$) between the tank bottom and the center-line of the bottom impeller is at least 0.35×$D_{bottom}$.

2. The method according to claim 1, wherein an agitation rate of the at least two impellers is at least 55 W/m³ and at most 85 W/m³.

3. The method according to claim 1, wherein the top impeller and the bottom impeller are hydrofoil impellers.

4. The method according to claim 1, wherein the hydrofoil impeller is a down-flowing impeller or an up-flowing impeller.

5. The method according to claim 1, wherein the at least one top impeller is a down-flowing axial hydrofoil impeller.

6. The method according to claim 1, wherein the top impeller is a three bladed hydrofoil design impeller.

7. The method according to claim 1, wherein the bottom impeller is a four pitched-bladed high solidity impeller.

8. The method according to claim 1, wherein a top impeller power number ($N_p$) is at least 0.1 and at most 0.9.

9. The method according to claim 1, wherein a bottom impeller power number ($N_p$) is at least 0.5 and at most 0.9.

10. The method according to claim 1, wherein a top impeller flow number (Nq) is at least 0.4 and at most 0.9.

11. The method according to claim 1, wherein an impeller to tank diameter ratio is at least 0.35 and at most 0.55.

12. The method according to claim 1, wherein a clearance ($S_c$) between the at least one sparger to the tank bottom is at least 0.17× sparger length ($S_L$), and wherein a clearance ($D_c$-$S_c$) between the at least one sparger to the center-line of the bottom impeller is 0.25× sparger length ($S_L$).

13. The method according to claim 1, wherein the bioreactor has a clearance ($S_c$) between the at least one sparger to the tank bottom of at least 315 mm and at most 360 mm, and wherein the bioreactor has a clearance ($D_c$-$S_c$) between the at least one sparger to the center-line of the bottom impeller of at least 180 mm and at most 205 mm.

14. The method according to claim 1, wherein the bioreactor has at least one baffle.

15. The method according to claim 14, wherein the bioreactor has a length of the at least one baffle at 1.1× a total straight height of the bioreactor (H), wherein the bioreactor has a width of the at least one baffle at 0.1× the internal diameter of the tank, and wherein the bioreactor has a height of the at least one baffle ($H_{baffle}$) at 1.1× the total straight height of the bioreactor (H)—a head height of the bioreactor ($H_h$).

16. The method according to claim 1, wherein the bioreactor has at least two ports for alkali addition.

17. The method according to claim 16, wherein said at least two ports are spatially separated from one another.

18. The method according to claim 17, wherein one port is located at the center-line of the bottom impeller and the other port is located at the center-line of the top impeller.

19. The method according to claim 1, wherein the bioreactor has a volume of at least 20000 l.

20. The method according to claim 19, wherein the bioreactor has at least one sparger, wherein a clearance ($S_c$) between the at least one sparger to the tank bottom is at least 560 mm and at most 620 mm, and wherein a clearance ($D_c$-$S_c$) between the at least one sparger to the center-line of the bottom impeller is at least 300 mm and at most 340 mm.

21. A method for cultivating and propagating mammalian cells, comprising:
   a) cultivating at least one mammalian cell under suitable conditions and in a suitable culture medium in a first bioreactor having a volume of at least 500 l,
   b) transferring cells from the medium containing the cells obtained by propagation of the at least one mammalian cell in the first bioreactor into a second bioreactor having a volume of at least 2000 l,
   c) cultivating the transferred cells in the second bioreactor,
   d) transferring the cells from the medium obtained in step c) into a third bioreactor having a volume of at least 10000 l, and
   e) cultivating the transferred cells in the third bioreactor,
   wherein the at least one of the first, second or third bioreactor is a bioreactor for the cultivation of mammalian cells, and wherein the at least one of the first, second or third bioreactor is a self-supporting biocompatible tank having a volume of at least 4000 l and at least one top impeller and at least one bottom impeller, and wherein the at least one top impeller is a hydrofoil impeller, and wherein an impeller spacing ($D_s$) between the top impeller and the bottom impeller is at least 1.229× the diameter of the bottom impeller ($D_{bottom}$) and at most 2×$D_{bottom}$, wherein a liquid height above the top impeller ($D_o$) is at least 0.3× the diameter of the top impeller ($D_{top}$) and at most 2.5×Dtop, and wherein a bottom clearance ($D_c$) between the tank bottom and the center-line of the bottom impeller is at least 0.35× $D_{bottom}$.

22. The method according to claim 21, wherein the cultivation-conditions are the same in the bioreactors of steps a), c) and e).

23. The method according to claim 21, wherein the first bioreactor has a volume of at least 1000 l.

24. The method according to claim 21, wherein the second bioreactor has a volume of at least 4000 l.

25. The method according to claim 21, wherein the third bioreactor has a volume of at least 20000 l.

26. The method according to claim 21, wherein the at least one of the first, second or third bioreactor is operated in a batch or a fed batch mode.

* * * * *